US011124799B2

(12) United States Patent
Howard et al.

(10) Patent No.: US 11,124,799 B2
(45) Date of Patent: Sep. 21, 2021

(54) PLANT-PRODUCED VACCINE COMPRISING AN AG2 POLYPEPTIDE FROM COCCIDIOIDES

(71) Applicant: Applied Biotechnology Institute, Inc., San Luis Obsipo, CA (US)

(72) Inventors: John Howard, San Luis Obispo, CA (US); Celine Hayden, San Louis Obispo, CA (US)

(73) Assignee: Applied Biotechnology Institute, Inc., San Luis Obsipo, CA (US)

( * ) Notice: Subject to any disclaimer, the term of this patent is extended or adjusted under 35 U.S.C. 154(b) by 0 days.

(21) Appl. No.: 16/439,301

(22) Filed: Jun. 12, 2019

(65) Prior Publication Data

US 2020/0009235 A1 Jan. 9, 2020

Related U.S. Application Data

(60) Provisional application No. 62/686,921, filed on Jun. 19, 2018.

(51) Int. Cl.
| | | |
|---|---|---|
| *C12N 15/82* | (2006.01) | |
| *A61K 39/00* | (2006.01) | |
| *C07K 14/37* | (2006.01) | |
| *C12N 15/62* | (2006.01) | |

(52) U.S. Cl.
CPC ...... *C12N 15/8257* (2013.01); *A61K 39/0002* (2013.01); *C07K 14/37* (2013.01); *C12N 15/62* (2013.01); *C12N 15/8234* (2013.01); *A61K 2039/57* (2013.01); *C07K 2319/55* (2013.01)

(58) Field of Classification Search
None
See application file for complete search history.

(56) References Cited

U.S. PATENT DOCUMENTS

2004/0001843 A1* 1/2004 Galgiani ................ C07K 14/37
424/185.1

OTHER PUBLICATIONS

Chan et al. Plant-made oral vaccines against human infectious diseases—are we there yet? (2015) Plant Biotechnol. J.; vol. 13; pp. 1056-1070 (Year: 2015).*
Yang et al. Cross-protective efficacy of dendritic cells targeting conserved influenze virus antigen expressed by Lactobacillus plantarum. (2016) Scientific Reports; vol. 6; pp. 1-20 (Year: 2016).*
"Synthetic construct partial ORF1 for hypothetical protein, peptide 3", GenBank: AJ544526.1, 1 page, Jul. 26, 2016.
"Synthetic construct partial ORF1 for hypothetical protein, peptide 12", GenBank: AJ544527.1, 1 page, Jul. 26, 2016.
"Synthetic construct partial ORF1 for hypothetical protein, peptide 18", GenBank: AJ544528.1,1 page, Jul. 26, 2016.
Cole et al., "Novel Strategies to Enhance Vaccine Immunity against Coccidioidomycosis", PLOS Pathogens, vol. 9, Issue 12, 4 pages, Dec. 2013.
Curiel et al., "Peptides Identified through Phage Display Direct Immunogenic Antigen to Dendritic Cells", The Journal of Immunology, vol. 172, pp. 7425-7431, 2004.
Delgado et al., "A Recombinant β-1,3-Gluoanosyltransferase Homolog of Coccidioides posadasii Protects Mice against Coccidioidomycosis", Infection and Immunity, vol. 71, No. 6, pp. 3010-3019, Jun. 2003.
Egelkrout et al., "Production of the bioscavenger butyrylcholinesterase in maize", Mol. Breeding, vol. 37, 12 pages Sep. 15, 2017.
Hayden et al., "Production of highly concentrated, heat-stable hepatitis B surface antigen in maize", Plant Biotechnology Journal, vol. 10, pp. 979-984, May 30, 2012.
Hayden et al., "Bioencapsulation of the hepatitis B surface antigen and its use as an effective oral immunogen", Vaccine, vol. 30(19), pp. 2937-2942, Apr. 19, 2012.
Hayden et al., "Maize-Produced Ag2 as a Subunit Vaccine for Valley Fever", The Journal of Infectious Diseases, 9 pages, Apr. 18, 2019.
Holwerda et al., "Proaleurain Vacuolar Targeting Is Mediated by Short Contiguous Peptide Interactions", The Plant Cell, vol. 4, pp. 307-318, Mar. 1992.
Hood et al., "Subcellular targeting is a key condition for high-level accumulation of cellulase protein in transgenic maize seed", Plant Biotechnology Journal, vol. 5, pp. 709-719, Jun. 1, 2007.
Hood et al., "Manipulating corn germplasm to increase recombinant protein accumulation", Plant Biotechnology Journal, vol. 10, pp. 20-30, 2012.
Howard et al., "Bioindustrial and Biopharmaceutical Products Produced in Plants", In Advances in Agronomy, 55 pages, 2005.
Hung et al., "Glucan-Chitin Particles Enhance Th17 Response and Improve Protective Efficacy of a Multivalent Antigen (rCpa1) against Pulmonary Coccidioides posadasii Infection", Infection and Immunity, vol. 86, Issue 11, 15 pages, Nov. 2018.
Hung et al., "Vaccine Immunity to Coccidioidomycosis Occurs by Early Activation of Three Signal Pathways to T Helper Cell Response (TH1, TH2, and TH17)", Infection and Immunity, vol. 79, No. 11, pp. 4511-4522, Nov. 2011.
Hurtgen et al., "Construction and Evaluation of a Novel Recombinant T Cell Epitope-Based Vaccine against Coccidioidomycosis", Infection and Immunity, vol. 80, No. 11, pp. 3960-3974, Nov. 2012.

(Continued)

*Primary Examiner* — Cathy Kingdom Worley
(74) *Attorney, Agent, or Firm* — McKee, Voorhees & Sease, PLC

(57) ABSTRACT

Vaccines, methods of producing, and methods of using are provided in which a protective response to Valley Fever disease is produced when administered to an animal. The vaccine provides for expression of *Coccidioides* sp. Ag2 polypeptide in a plant or plant part, linked to a promoter preferentially directing expression to seed tissue of the plant or plant part. Further embodiments provide the polypeptide is targeted to the cell wall, vacuole or endoplasmic reticulum. The polypeptide may be fused to a dendritic cell targeting dendritic cell or a heat labile enterotoxin. Increased expression levels in the plant or plant part are obtained. The vaccine comprising the plant-produced Ag2 polypeptide may be a glucan chitin particle comprising the Ag2 polypeptide. The plant or plant materials in an embodiment may be orally administered.

14 Claims, 8 Drawing Sheets

Specification includes a Sequence Listing.

(56) References Cited

OTHER PUBLICATIONS

Lamphear et al., "Delivery of subunit vaccines in maize seed", Journal of Controlled Release, vol. 85, pp. 169-180, Mar. 1, 2002.
Lamphear et al., "A corn-based delivery system for animal vaccines: an oral transmissible gastroenteritis virus vaccine boosts lactogenic immunity in swine", Vaccine, vol. 22, pp. 2420-2424, 2004.
Lappalainen et al., "Protection against live rotavirus challenge in mice induced by parenteral and mucosal delivery of VP6 subunit rotavirus vaccine", Arch. Virol., vol. 160, pp. 2075-2078, May 20, 2015.
"*E. coli* (from human) heat-labile enterotoxin subunit B gene (eltB), complete cds", GenBank: M17874.1, 1 pages, Apr. 21, 1996.
Mirza et al., "Beta-Glucan Particles as Vaccine Adjuvant Carriers", Vaccines for Invasive Fungal Infections: Methods and Protocols, Methods in Molecular Biology, vol. 1625, Ch. 11, pp. 143-157, 2017.
Mohamadzadeh et al., "Dendritic cell targeting of Bacillus anthracis protective antigen expressed by Lactobaccillus acidophilus protects mice from lethal challenge", PNAS, vol. 106, No. 11, pp. 4331-4336, Mar. 17, 2009.
Rosales-Mendoza et al., "Expression of an *Escherichia coli* antigenic fusion protein comprising the heat labile toxin B subunit and the heat stable toxin, and its assembly as a functional oligomer in transplastsomic tobacco plants", The Plant Journal, vol. 57, pp. 45-54, 2009.
Russell et al., "Tissue-specific expression in transgenic maize of four endosperm promoters from maize and rice", Transgenic Research, vol. 6, pp. 157-168, 1997.
Shubitz et al., "Improved protection of mice against lethal respiratory infection with Coccidioides posadasii using two recombinant antigens expressed as a single protein", Vaccine, vol. 24, pp. 5904-5911, Apr. 4, 2006.
Streatfield et al., "Corn as a production system for human and animal vaccines", Vaccine, vol. 21, pp. 812-815, 2003.
Streatfield et al., "Plant-based vaccines: unique advantages", Vaccine, vol. 19, pp. 2742-2748, 2001.
Streatfield, Stephen, "Mucosal immunization using recombinant plant-based oral vaccines", Methods, vol. 38, pp. 150-157, 2006.
Subramanya et al., "Enhanced Induction of HIV-specific Cytotoxic T Lymphocytes by Dendritic Cell-targeted Delivery of SOCS-1 siRNA", www.moleculartherapy.org, vol. 18, No. 11, pp. 2028-2037, Nov. 2010.
Tacket et al., "Immunogenicity of recombinant LT-B delivered orally to humans in transgenic corn", Vaccine, vol. 22, pp. 4385-4389, Jan. 6, 2004.
Tarcha et al., "Multivalent Recombinant Protein Vaccine against Coccidioidomycosis", Infection and Immunity, vol. 74, No. 10, pp. 5802-5813, Oct. 2006.
"Coccidioides immitis antigen 2 (Ag2) mRNA, complete cds", GenBank: U32518.1, 2 pages, Nov. 4, 1996.
"Coccidioides immitis immunoreactive cell wall protein mRNA, complete cds", GenBank: U39835.1, 1 page, Jan. 18, 1996.
Wu et al., "Immunization of Chickens with VP2 Protein of Infectious Bursal Disease Virus Expressed in *Arabidopsis thaliana*", Avian Diseases, vol. 48, pp. 663-668, May 3, 2004.
"Proline-rich antigen [Coccidioides immitis RS]", NCBI Reference Sequence: XP_001240075.1, 2 pages, Oct. 10, 2017.
"Proline-rich antigen [Coccidioides posadasii C735 delta SOWgp]", NCBI Reference Sequence: XP_003069153.1, 2 pages, Apr. 17, 2018.
Zhu et al., "Molecular Cloning and Characterization of Coccidioides immitis Antigen 2 cDNA", Infection and Immunity, vol. 64, No. 7, pp. 2695-2699, Jul. 1996.

* cited by examiner

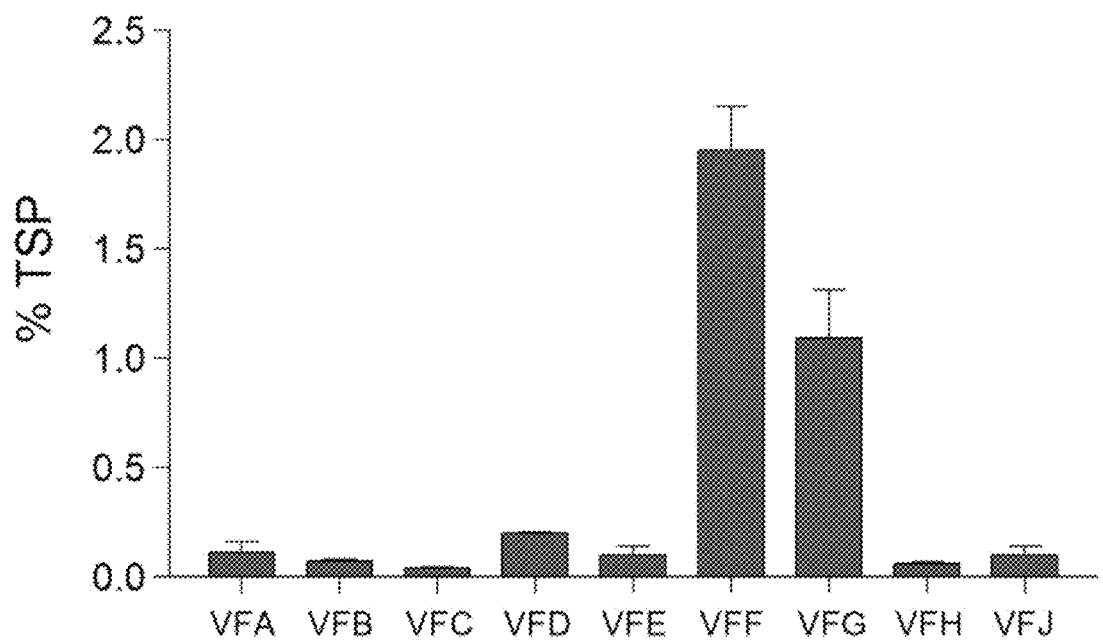
FIG. 3A
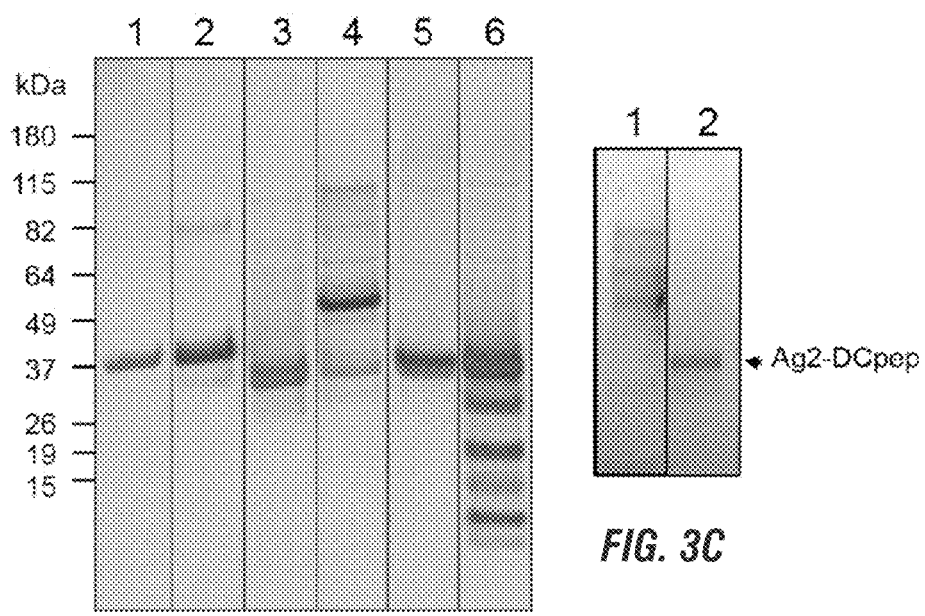
FIG. 3B
FIG. 3C

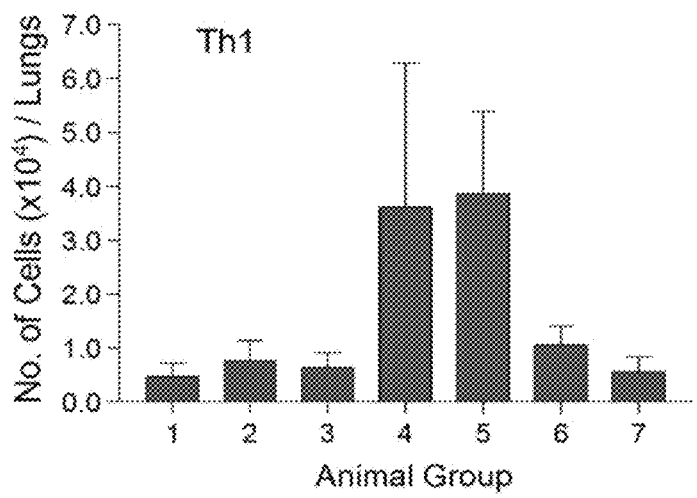
FIG. 5A
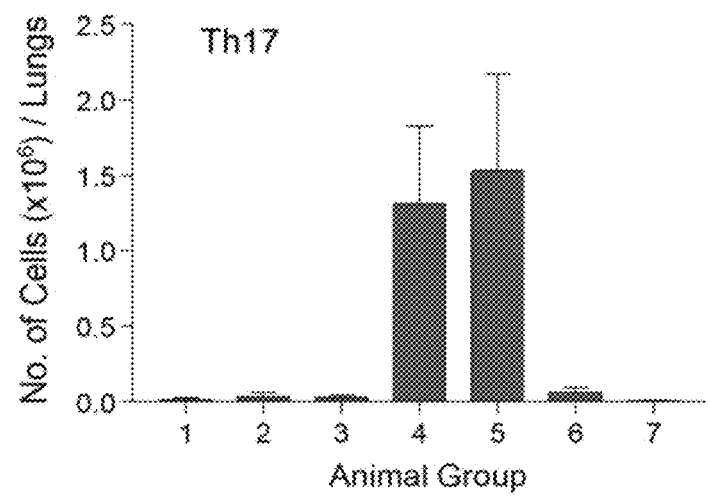
FIG. 5B
FIG. 5C

PLANT-PRODUCED VACCINE COMPRISING AN AG2 POLYPEPTIDE FROM COCCIDIOIDES

CROSS-REFERENCE TO RELATED APPLICATION

This application claims priority under 35 U.S.C. § 119 to provisional application U.S. Ser. No. 62/686,921, filed Jun. 19, 2018, the contents of which are incorporated herein by reference in their entirety.

STATEMENT REGARDING FEDERALLY SPONSORED RESEARCH

This invention was made with Government support under contract (Contract No. HHSN272201600035C), NIH MARC T34-GM008574 (JEG) awarded by National Institute of Allergy and Infectious Diseases, part of the National Institutes of Health. The Government has certain rights in this invention.

SEQUENCE LISTING

The instant application contains a Sequence Listing which has been submitted in ASCII format via EFS-Web and is hereby incorporated by reference in its entirety. Said ASCII copy, created on Jun. 5, 2019 is named P12619US01_SEQ_LISTING_06-05-2019.txt and is 29,486 bytes in size.

BACKGROUND

Vaccination programs greatly reduce mortality and morbidity rates and are, by far, the most cost-effective strategy for combating infectious diseases[1, 2]. Set against the costs of diagnosis and treatment, and additional costs incurred through lost productivity of infected individuals, vaccination is clearly highly cost-effective. Safe and effective vaccines have been developed against many infectious diseases, but fungal diseases are conspicuously absent from the roster of vaccine-targeted pathogens, despite $2.6 billion in direct healthcare costs spent annually to fight fungal infections in the United States[3]. It is the aim of this research program to produce the first commercially available fungal vaccine, targeted to *Coccidioides*. Such a vaccine could act as the blueprint for preventing other important fungal diseases. *Coccidioides immitis* and *C. posadasii* are endemic to the soils of the arid and semi-arid regions of the southwestern United States, as well as other semi-desert areas of the Americas. Humans and other mammals living in, or traveling to, the endemic regions inhale the airborne *Coccidioides* spores through the nasal passage, which can lead to coccidioidomycosis, otherwise known as San Joaquin Valley Fever. Attack rates are estimated to be 11% for Caucasians, 54% for African-Americans, 67% for Filipinos, and 36% for Asians[4]. While 60% of infections are asymptomatic, the remaining 40% result in pulmonary disease that mimics flu-like symptoms[5]. Encouragingly, individuals who have recovered from symptomatic coccidioidomycosis achieve life-long immunity to recurrent *Coccidioides* infections[6, 7]. Unfortunately, symptomatic infections lead to chronic disease in 5% of cases and extrapulmonary dissemination of the fungi in 1% of cases[8]. These severe and chronic cases often require week-long hospitalization, long-term administration of harsh anti-fungal therapeutics, and result in fatalities in 1.5% of pediatric patients[9]. In the state of Arizona alone, coccidioidomycosis incurred an estimated $86 million in hospitalization costs in 2007[6], a cost that is likely rising with the alarming increased incidence of the disease[10]. Approximately 10% of the US population lives in the Southwest, more than 300,000 military personnel trained in these areas, and numerous visitors pass through the Southwest or overwinter during the coolest winter months[11]. An estimated 150,000 new infections occur each year in the United States[8] and the incidence of reported cases has increased 8-fold since 1998[10]. Based on 2014 U.S. census data, an estimated 41.7 million individuals live in *Coccidioides* endemic areas[6, 12], which represents approximately 13% of the U.S. population with many more people at risk for exposure. In 2014, an additional 40.7 million travelers visited Arizona, 41.1 million visited Las Vegas, Nev., and 16.1 million international travelers visited destinations in California[13-15]. For the significant population base that lives in, undergoes military training in, or travels to these desirable warm weather areas, a vaccine would be highly desirable.

BRIEF SUMMARY

Provided are vaccines and methods of use for protecting an animal from Valley Fever. Embodiments provide a method of expressing a polypeptide of *Coccidioides* sp. by introducing into a plant a seed tissue preferred promoter, a nucleic acid molecule encoding an Ag2 polypeptide of *Coccidioides* linked to the promoter and expressing the Ag2 polypeptide. Further embodiments provide for targeting expression of the polypeptide to the cell wall, vacuole or endoplasmic reticulum. Still further embodiments provided the Ag2 polypeptide is fused to a dendritic cell targeting dendritic cell peptide, or a heat labile enterotoxin B subunit peptide. Additional embodiments provide the vaccine comprises glucan particles comprising an Ag2 polypeptide, and the vaccine may comprise glucan chitin particles or glucan particles and chitin. The methods provide for expression in a plant or plant part of at least 100 mg/kg or greater. Vectors, plants comprising the vectors and methods of producing a protective response in an animal to Valley Fever are provided. Oral administration of plant material comprising the Ag2 polypeptide so produced are provided in certain embodiments.

BRIEF DESCRIPTION OF THE DRAWINGS

FIGS. 3 A, B and C is a graph (A) showing quantification of Ag2 production in maize. Accumulation of Ag2 proteins in top 10% of T1 seeds from each of the nine Ag2-gene-construct transformed maize lines was measured and presented as percent TSP (mean±standard error). B and C are Western blots showing analysis of maize-derived recombinant Ag2 proteins. Proteins were separated by gel electrophoresis, transferred to nitrocellulose membrane and probed with an anti-Ag2 antibody. (B) Protein samples were from the E. coli expressed recombinant Ag2 (1 µg, lane 1; 5 µg, lane 2) or crude seed extracts from VFE (lane 3), VFF (lane 4), VFG (lane 5) and VFH (lane 6) transformed corn lines. (C) Proteins were isolated from un-transformed (lane 1) or VFG (lane 2) transformed corn seeds by anti-Ag2 affinity chromatography. The detection of Ag2-DCpep (~35 kDa) isolated from VFG seeds was indicated with an arrow.

FIGS. 5A, B and C are an image (A) and graphs (B) (C) showing increase of Th17 cells in the lungs of Ag2-vaccinated mice following FKS challenge. Flow cytometric analysis of IFN-γ- and IL-17A-expressing Th1 and Th17 cells, respectively in lungs of mice that were vaccinated with various Ag2 formulations and challenged with formalin-killed-spherule (FKS) of Coccidioides posadasii. Bacterium-expressed recombinant Ag2 encapsulated with glucan-chitin-particles (GCP-Ag2b) and 3 types of maize-derived Ag2 in the form of edible wafers (VFE, VFF and VFG) were used for vaccine priming (p) and/or boosting (b) 3 times at 2 weeks apart. GCP-OVA, wafer contained no Ag2 (corn ctl.) and PBS alone were used for mock vaccination. The percentages of gated, specific IL-17A producing cells per lung organ (panel A) and the numbers of Th1 (CD4+IFN-γ+; panel B) and Th17 (CD4+IL-17A+; panel C) cells, were determined by intracellular cytokine staining 7 days post FKS challenge.

DESCRIPTION

Figure 1:
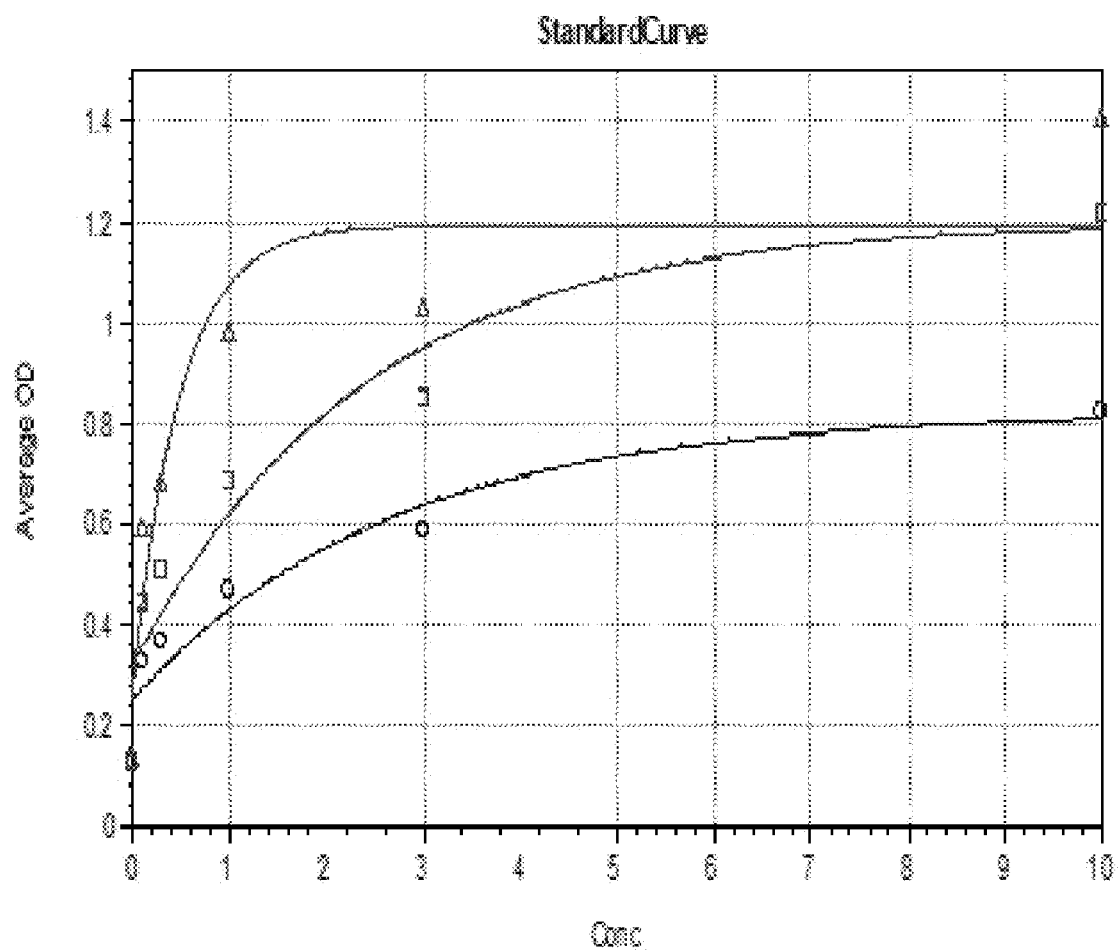
FIG. 1 is a graph showing results of a sandwich ELISA and extraction of Ag2 from maize grain. Various concentrations of the reagents were used to optimize the ELISA for detection of Ag2. The results represent the effect that the concentration of the biotinylated antibody has on the OD (y-axis) in relation to nanograms of Ag2 (x-axis). Triangles are the highest concentration, circles the lowest and squares in-between concentration. The signal to noise ratio is useable in all cases but the middle concentration was selected for routine use.

Coccidioides offers several advantages as a model fungal pathogen for successful vaccine development. Natural infection with Coccidioides leads to life-long protection[8], indicating that a vaccine could induce a protective response that would be long-lasting. In addition, several antigens have been identified that provide protection to mice when challenged with a potentially lethal dose of this pathogen[4, 16-19]. The lead vaccine candidate, Ag2 has shown high efficacy in C57BL/6 mouse model challenge. There are also new versions of Ag2 under investigation that show promise (Dr. Hung, submitted manuscript). Glucan-Chitin Particles Enhance Th17 Response and Improve Protective Efficacy of a Multivalent Antigen (rCpa1) against Pulmonary Coccidioides posadasii Infection Chiung-Yu Hung, Hao Zhang, Natalia Castro-Lopez, Gary R. Ostroff, Payam Khoshlenar, Ambily Abraham, Garry T. Cole, Austin Negron, Thomas Forsthuber, Tao Peng, John N. Galgiani, Neil M. Ampel, Jieh-Juen Yu Infection and Immunity October 2018, 86 (11) e00070-18; DOI: 10.1128/IAI.00070-18

Despite the fact the lead antigen shows efficacy, there are still several hurdles limiting the development of this candidate as a vaccine. The foremost problem is that Ag2 is a glycosylphosphatidylinisotol (GPI)-anchored protein with a high concentration of proline and cysteine residues, and as such is difficult to express in many traditional recombinant protein production systems. Expression in E. coli can reach 8 mg/L (Dr. Chiung-Yu Hung, personal communication), while in yeast it can reach 10 mg/L (Dr. Tao Peng, personal communication). This is consistent with yields obtained in our own lab from E. coli, but these levels are far below the levels necessary to achieve cost targets where typical commercial protein products reach levels of grams/L.

The second hurdle is to administer the vaccine in a manner that will elicit an immune response that can provide protection. Many traditional vaccines are administered parenterally and while providing a robust systemic response, these frequently provide little or no mucosal response. In the case of Valley Fever there is no correlation with sera antibodies and protection however, there is a correlation with antibodies from mucosal tissues.

As discussed herein the vaccine and methods are to a Coccidioides antigen 2 (Ag2) polypeptide produced in a plant and which may be used as a vaccine to provide a protective response to Valley Fever. The antigen is a T-cell reactive component of mycelia and spherule cell walls. See Ahu et al. (1996) "Molecular cloning and characterization of Coccidioides immitis antigen 2 cDNA" Infect. Immun. 64(7):2695-9. The protein has a predicted molecular mass, as per Zhu et al. of 19.5 kDa and has an amino acid terminus of 18 residues that was identified as a signal peptide. The protein was shown to have reactivity with sera from patients having coccidioidomycosis. It also elicited delayed-type footpad hypersensitivity responses in Coccidioides immune mice.

The Ag2 nucleic acid molecule used in the experiments below was the following (SEQ ID NO: 1); see also the 1234 base pair Genbank U32518.1 (SEQ ID NO: 8) or U39835.1

(SEQ ID NO: 9). The coding sequence for U32518.1 is from bases 175-759 (SEQ ID NO: 18). The encoded protein is SEQ ID NO: 10.

SEQ ID NO: 1 encodes the polypeptide SEQ ID NO: 2. See XP_003069153.1 (SEQ ID NO: 10) or XP_001240075.1 (SEQ ID NO: 11) and note that the first amino acid can vary and be M instead of V (See SEQ ID NO: 2 and 10).

In the present methods it was found that unexpectedly high expression levels were achieved. When referring to the Ag2 sequence is intended to include a non-optimized or optimized sequence that has minor variations not detracting from its ability to induce a protective response as a result of optimization.

An embodiment provides the Ag2 polypeptide is fused to a dendritic cell targeting sequence, (DC), and/or a heat labile enterotoxin B subunit (LtB) peptide. Dendritic cells are antigen-presenting cells that participate in activation of T cells. Polypeptides may be targeted to dendritic cells. See Mohamadzadeh et al. (2009) "Dendritic cell targeting of *Bacillus anthracis* protective antigen expressed by *Lactobacillus acidophilus* protects mice from lethal challenge" Proc. Natl. Acad. Sci USA 106, 4331-4336. However, they also have a negative feedback interaction to suppress the impact on activation to prevent an excessive response. See, e.g., Subramanya et al. (2010)"Enhanced induction of HIV-specific cytotoxic T lymphocytes by dendritic cell-targeted delivery of SOCS-1 siRNA" www.moleculartherapy.org. vol. 18 No. 11, 2028-2037. Dendritic cell targeting sequences may be identified, for example, by using a phage display peptide library that specifically binds to a ligand expressed on DCs. See, e.g., Curiel et al. (2004) "Peptides identified through phage display direct immunogenic antigen to dendritic cells" J. Immuno. 15; 172(12):7425-31 using such a system to identify EMBL Nucleotide Database Accession No. AJ544526, AJ544527 and AJ544528. In one embodiment of the invention a fusion peptide is created at the Ag2 C-terminus with a DC3 peptide. The twelve amino acid peptide is FYPSYHSTPQRP (SEQ ID NO: 3). In an embodiment a nucleic acid molecule encoding the peptide is provided and may be SEQ ID NO: 4. Another embodiment provides for fusion with the non-toxic subunit for *Escherichia coli* labile toxin, LTB. See Rosales-Mendoza et al. (2009) "Expression of an *Escherichia coli* antigenic fusion protein comprising the heat labile toxin B subunit and the heat stable toxin, and its assembly as a functional oligomer in transplastomic tobacco plant" The Plant Journal 57, 45-54. Used in the experiments below was the following sequence which includes a linker shown in italics (SEQ ID NO: 5) adjacent the LtB sequence (SEQ ID NO: 6).

```
gtcgacccgagggtgccgagctccggcgccccgcagtccatcaccgagct ctgctccgagtaccacaacacccagatctacaccatcaacgacaagatcc tctcctacaccgagagcatggccggcaagcgcgagatggtgatcatcacc ttcaagtccggcgccaccttccaggtggaggtgccgggctcccagcacat cgactcccagaagaaggccatcgagcgcatgaaggacaccctccgcatca cctacctcaccgagaccaagatcgacaagctctgcgtgtggaacaacaag accccgaactccatcgccgccatcagcatggagaac
```

The LtB sequence encodes SEQ ID NO: 7.

As discussed more fully below, an embodiment provides for a glucan particle or a glucan particle and chitin or a glucan chitin particle (GCP) and the antigen may be loaded into the particle. These particles are porous shells with a hollow core. The polypeptide may be loaded with a carrier protein in one example. An example provided by Cole et al. describes loading the polypeptide with a carrier and interacting with yeast RNA within the core to form an antigen complex of a size that does not permit diffusion out through the shell. See Cole et al. (2013) "Novel strategies to enhance vaccine immunity against coccidiodomycosis" *PLoS pathogens* 9 e1003768.

Using the compositions and methods described here, a plant may be produced that expresses Ag2 at high levels. Such levels in an embodiment are at least ten fold higher than those produced in microbes. In another embodiment the levels produced are at or greater than 10 mg/kg, 15 mg/kg, 20 mg/kg, 25 mg/kg, 30 mg/kg, 35 mg/kb, 40 mg/kg, 45 mg/kg and in further embodiments can be at least 50 mg/kg, 55 mg/kg or more, or amounts in-between. Another embodiment provides the expression is greater than 10 mg/kg, in further embodiments is at least 60 mg/kg and amounts in between. Still further embodiments provide for expression levels of at least 1% total soluble protein (TSP), 2% TSP, 3% TSP, 4% TSP or more or amounts in-between.

The term plant or plant material or plant part is used broadly herein to include any plant at any stage of development, or to part of a plant, including a plant cutting, a plant cell, a plant cell culture, a plant organ, a plant seed, and a plantlet. A plant cell is the structural and physiological unit of the plant, comprising a protoplast and a cell wall. A plant cell can be in the form of an isolated single cell or aggregate of cells such as a friable callus, or a cultured cell, or can be part of a higher organized unit, for example, a plant tissue, plant organ, or plant. Thus, a plant cell can be a protoplast, a gamete producing cell, or a cell or collection of cells that can regenerate into a whole plant. As such, a seed, which comprises multiple plant cells and is capable of regenerating into a whole plant, is considered a plant cell for purposes of this disclosure. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, roots, and the like. A part of a plant useful for propagation includes, for example, seeds, fruits, cuttings, seedlings, tubers, rootstocks, and the like. The tissue culture will preferably be capable of regenerating plants. Preferably, the regenerable cells in such tissue cultures will be embryos, protoplasts, meristematic cells, callus, pollen, leaves, anthers, roots, root tips, silk, flowers, kernels, ears, cobs, husks or stalks. Still further, provided are plants regenerated from the tissue cultures.

When using the germ (embryo) of the plant, one can separate the germ from the remainder of the seed and use it as a source of the Ag2. Methods of using germ as the source of protein are discussed at U.S. Pat. Nos. 7,179,961 and 6,504,085 incorporated herein by reference in their entirety.

A "construct" is a package of genetic material inserted into the genome of a cell via various techniques. A "vector" is any means for the transfer of a nucleic acid into a host cell. A vector may be a replicon to which a DNA segment may be attached so as to bring about the replication of the attached segment. A "replicon" is any genetic element (e.g., plasmid, phage, cosmid, chromosome, virus) that functions as an autonomous unit of DNA or RNA replication in vivo, i.e., capable of replication under its own control. In addition to a nucleic acid, a vector may also contain one or more regulatory regions, and/or selectable markers useful in selecting, measuring, and monitoring nucleic acid transfer results (transfer to which tissues, duration of expression, etc.).

A "cassette" refers to a segment of DNA that can be inserted into a vector at specific restriction sites. The segment of DNA encodes a polypeptide of interest or produces RNA, and the cassette and restriction sites are designed to ensure insertion of the cassette in the proper reading frame for transcription and translation.

A cell has been "transfected" by exogenous or heterologous DNA or RNA when such DNA or RNA has been introduced inside the cell.

When referring to a nucleic acid molecule encoding Ag2, is intended to include by way of example, a nucleic acid molecule that encodes the Ag2 protein and variants and fragments thereof. Variants and fragments retain the ability to produce a protective response to Valley Fever.

As used herein, the terms nucleic acid or polynucleotide refer to deoxyribonucleotides or ribonucleotides and polymers thereof in either single- or double-stranded form. As such, the terms include RNA and DNA, which can be a gene or a portion thereof, a cDNA, a synthetic polydeoxyribonucleic acid sequence, or the like, and can be single-stranded or double-stranded, as well as a DNA/RNA hybrid. Furthermore, the terms are used herein to include naturally-occurring nucleic acid molecules, which can be isolated from a cell, as well as synthetic molecules, which can be prepared, for example, by methods of chemical synthesis or by enzymatic methods such as by the polymerase chain reaction (PCR). Unless specifically limited, the terms encompass nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) *Nucleic Acid Res.* 19:5081; Ohtsuka et al. (1985) *J. Biol. Chem.* 260:2605-2608; Rossolini et al. (1994) *Mol. Cell. Probes* 8:91-98). The term nucleic acid is used interchangeably with gene, cDNA, and mRNA encoded by a gene.

As used herein, a nucleotide segment is referred to as operably linked when it is placed into a functional relationship with another nucleic acid segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Operably linked elements may be contiguous or non-contiguous. When used to refer to the joining of two protein coding regions, by operably linked it is intended that the coding regions are in the same reading frame. Alternatively, the additional gene(s) can be provided on multiple expression cassettes. Such an expression cassette is provided with a plurality of restriction sites and/or recombination sites for insertion of the polynucleotide to be under the transcriptional regulation of the regulatory regions.

Nucleic acids include those that encode an entire polypeptide or fragment thereof. The invention includes not only the exemplified nucleic acids that include the nucleotide sequences as set forth herein, but also nucleic acids that are substantially identical to, correspond to, or substantially complementary to, the exemplified embodiments. For example, the invention includes nucleic acids that include a nucleotide sequence that is at least about 70% identical to one that is set forth herein, more preferably at least 75%, still more preferably at least 80%, more preferably at least 85%, 86%, 87%, 88%, 89% still more preferably at least 90%, 91%, 92%, 93%, 94%, and even more preferably at least about 95%, 96%, 97%, 98%, 99%, 100% identical (or any percentage in between) to an exemplified nucleotide sequence. The nucleotide sequence may be modified as described previously, so long any antigenic polypeptide encoded is capable of inducing the generation of a protective response.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent substitutions" or "silent variations," which are one species of "conservatively modified variations." Every polynucleotide sequence described herein which encodes a polypeptide also describes every possible silent variation, except where otherwise noted. Thus, silent substitutions are an implied feature of every nucleic acid sequence which encodes an amino acid. One of skill will recognize that each codon in a nucleic acid (except AUG, which is ordinarily the only codon for methionine) can be modified to yield a functionally identical molecule by standard techniques. In some embodiments, the nucleotide sequences that encode a protective polypeptide are preferably optimized for expression in a particular host cell (e.g., yeast, mammalian, plant, fungal, and the like) used to produce the polypeptide or RNA.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" referred to herein as a "variant" where the alteration results in the substitution of an amino acid with a chemically similar amino acid. Conservative substitution tables providing functionally similar amino acids are well known in the art. See, for example, Davis et al., "Basic Methods in Molecular Biology" Appleton & Lange, Norwalk, Conn. (1994). Such conservatively modified variants are in addition to and do not exclude polymorphic variants, interspecies homologs, and alleles.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, 1984, Proteins).

The isolated variant proteins can be purified from cells that naturally express it, purified from cells that have been altered to express it (recombinant), or synthesized using known protein synthesis methods. For example, a nucleic acid molecule encoding the variant polypeptide is cloned into an expression vector, the expression vector introduced into a host cell and the variant protein expressed in the host cell. The variant protein can then be isolated from the cells by an appropriate purification scheme using standard protein purification techniques.

A protein is comprised of an amino acid sequence when the amino acid sequence is at least part of the final amino acid sequence of the protein. In such a fashion, the protein may be an original polypeptide, a variant polypeptide and/or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids.

The variant proteins used in the present invention can be attached to heterologous sequences to form chimeric or fusion proteins. Such chimeric and fusion proteins comprise a variant protein fused in-frame to a heterologous protein having an amino acid sequence not substantially homologous to the variant protein. The heterologous protein can be fused to the N-terminus or C-terminus of the variant protein.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., eds. (1995) *Current Protocols in Molecular Biology* (Greene Publishing and Wiley-Interscience, New York). Moreover, many expression vectors are commercially available that already encode a fusion moiety (e.g., a GST protein). A variant protein-encoding nucleic acid can be cloned into such an expression vector such that the fusion moiety is linked in-frame to the variant protein.

Polypeptides sometimes contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art. Accordingly, the variant peptides of the present invention also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Fragments of the variant proteins may be used, in addition to proteins and peptides that comprise and consist of such fragments, provided that such fragments act as an antigen and/or provide treatment for and/or protection against infections as provided by the present invention.

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1.0 M NaCl, 1% SDS at 37° C., and a wash in 0.1×SSC at 60 to 65° C.

Specificity is also the function of post-hybridization washes, the critical factors being the ionic strength and temperature of the final wash solution. For DNA-DNA hybrids, the $T_m$ can be approximated from the equation $T_m = 81.5°$ C. $+ 16.6$ (log M) $+ 0.41$(% GC) $- 0.61$(% form.) $- 500/L$, where M is the molarity of monovalent cations, % GC is the percentage of guanosine and cytosine nucleotides in the DNA, % form is the percentage of formamide in the hybridization solution, and L is the length of the hybrid in base pairs (Meinkoth and Wahl, 1984). The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted for sequences of the desired identity to hybridize. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11 to 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Ausubel et al., eds. (1995) *Current Protocols in Molecular Biology* (Greene Publishing and Wiley-Interscience, New York) and Sambrook et al., (1989) *Molecular Cloning: A Laboratory Manual*, 2nd Edition. Cold Spring Harbor Laboratory Press, Plainview, N.Y.

The following terms are used to describe the sequence relationships between two or more nucleic acids or polynucleotides: (a) "reference sequence", (b) "comparison window", (c) "sequence identity" and (d) "percentage of sequence identity."

(a) As used herein, "reference sequence" is a defined sequence used as a basis for sequence comparison. A reference sequence may be a subset or the entirety of a specified sequence; for example, as a segment of a full-length promoter sequence, or the complete promoter sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to accurately reflect the similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Optimal alignment of sequences for comparison can use any means to analyze sequence identity (homology) known in the art, e.g., by the progressive alignment method of termed "PILEUP" (Morrison, Mol. Biol. Evol. 14:428-441 (1997), as an example of the use of PILEUP); by the local homology algorithm of Smith & Waterman (Adv. Appl. Math. 2: 482 (1981)); by the homology alignment algorithm of Needleman & Wunsch (J. Mol. Biol. 48:443 (1970)); by the search for similarity method of Pearson (Proc. Natl. Acad. Sci. USA 85: 2444 (1988)); by computerized implementations of these algorithms (e.g., GAP, BEST FIT, FASTA, and TFASTA in the Wisconsin Genetics Software Package, Genetics Computer Group, 575 Science Dr., Madison, Wis.); ClustalW (CLUSTAL in the PC/Gene program by Intelligenetics, Mountain View, Calif., described by, e.g., Higgins, Gene 73: 237-244 (1988); Corpet, Nucleic Acids Res. 16:10881-10890 (1988); Huang, Computer Applications in the Biosciences 8:155-165 (1992); and Pearson, Methods in Mol. Biol. 24:307-331 (1994); Pfam (Sonnhammer, Nucleic Acids Res. 26:322-325 (1998); TreeAlign (Hein, Methods Mol. Biol. 25:349-364 (1994); MEG-ALIGN, and SAM sequence alignment computer programs; or, by manual visual inspection.

Another example of algorithm that is suitable for determining sequence similarity is the BLAST algorithm, which is described in Altschul et al, J. Mol. Biol. 215: 403-410 (1990). The BLAST programs (Basic Local Alignment Search Tool) of Altschul, S. F., et al., (1993) J. Mol. Biol. 215:403-410) searches under default parameters for identity to sequences contained in the BLAST "GENEMBL" database. A sequence can be analyzed for identity to all publicly available DNA sequences contained in the GENEMBL database using the BLASTN algorithm under the default parameters.

Software for performing BLAST analyses is publicly available through the National Center for Biotechnology Information, www.ncbi.nlm.nih.gov/; see also Zhang, Genome Res. 7:649-656 (1997) for the "PowerBLAST" variation. This algorithm involves first identifying high scoring sequence pairs (HSPs) by identifying short words of length W in the query sequence that either match or satisfy some positive valued threshold score T when aligned with a word of the same length in a database sequence. T is referred to as the neighborhood word score threshold (Altschul et al, J. Mol. Biol. 215: 403-410 (1990)). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff, Proc. Natl. Acad. Sci. USA 89:10915-10919 (1992)) alignments (B) of 50, expectation (E) of 10, M=5, N=-4, and a comparison of both strands. The term BLAST refers to the BLAST algorithm which performs a statistical analysis of the similarity between two sequences; see, e.g., Karlin, Proc. Natl. Acad. Sci. USA 90:5873-5787 (1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

In an embodiment, GAP (Global Alignment Program) can be used. GAP uses the algorithm of Needleman and Wunsch J. Mol. Biol. 48:443-453 (1970) to find the alignment of two complete sequences that maximizes the number of matches and minimizes the number of gaps. Default gap creation penalty values and gap extension penalty values in the commonly used Version 10 of the Wisconsin Package® (Accelrys, Inc., San Diego, Calif.) for protein sequences are 8 and 2, respectively. For nucleotide sequences the default gap creation penalty is 50 while the default gap extension penalty is 3. Percent Similarity is the percent of the symbols that are similar. Symbols that are across from gaps are ignored. A similarity is scored when the scoring matrix value for a pair of symbols is greater than or equal to 0.50, the similarity threshold. A general purpose scoring system is the BLOSUM62 matrix (Henikoff and Henikoff, Proteins, 17: 49-61 (1993)), which is currently the default choice for BLAST programs. BLOSUM62 uses a combination of three matrices to cover all contingencies. Altschul, J. Mol. Biol. 36: 290-300 (1993), herein incorporated by reference in its entirety and is the scoring matrix used in Version 10 of the Wisconsin Package® (Accelrys, Inc., San Diego, Calif.) (see Henikoff & Henikoff (1989) Proc. Natl. Acad. Sci. USA 89:10915).

As used herein, "sequence identity" or "identity" in the context of two nucleic acid sequences makes reference to the residues in the two sequences that are the same when aligned for maximum correspondence over a specified comparison window.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

Identity to a sequence used herein would mean a polynucleotide sequence having at least 65% sequence identity, more preferably at least 70% sequence identity, more preferably at least 75% sequence identity, more preferably at least 80% identity, more preferably at least 85% 86%, 87%, 88%, 89%, 90%, 91%, 92%, 93%, 94%, 95%, 96%, 97%, 98%, 99% sequence identity.

A nucleic acid molecule may be combined with any number of other components to be introduced into the plant, including combined with another nucleic acid molecule of interest to be expressed in the host. The "nucleic acid molecule of interest" refers to a nucleotide sequence that encodes for another desired polypeptide or protein but also may refer to nucleotide sequences that do not constitute an entire gene, and which do not necessarily encode a polypeptide or protein. For example, when used in a homologous recombination process, the nucleic acid molecule may be placed in a construct with a sequence that targets and area of the chromosome in the plant but may not encode a protein. The gene can be used to drive mRNA that can be used for a silencing system, such as antisense, and in that instance, no protein is produced. Means of increasing or inhibiting a protein are well known to one skilled in the art and, by way of example, may include, transgenic expression, antisense suppression, co-suppression methods including but not limited to: RNA interference, gene activation or suppression using transcription factors and/or repressors, mutagenesis including transposon tagging, directed and site-specific mutagenesis, chromosome engineering and, homologous recombination. In the case of use with homologous recombination, no in vivo construct will be required. If desired, a nucleic acid molecule of interest can be optimized for host or other plant translation by optimizing the codons used for host or plants and the sequence around the translational start site for host or plants. Sequences resulting in potential mRNA instability can also be avoided.

In general, the methods available for construction of recombinant genes, optionally comprising various modifications for improved expression, can differ in detail and any of the methods available to one skilled in the art may be used in the invention. However, conventionally employed methods include PCR amplification, or the designing and synthesis of overlapping, complementary synthetic oligonucleotides, which are annealed and ligated together to yield a gene with convenient restriction sites for cloning, or subcloning from another already cloned source, or cloning from a library. The methods involved are standard methods for a molecular biologist (Sambrook et al., (1989) *Molecular Cloning: A Laboratory Manual*, 2nd Edition. Cold Spring Harbor Laboratory Press, Plainview, N.Y.).

Once the gene is engineered to contain desired features, such as the desired subcellular localization sequences, it may then be placed into an expression vector by standard methods. The selection of an appropriate expression vector will depend upon the method of introducing the expression vector into host cells. A typical expression vector contains prokaryotic DNA elements coding for a bacterial origin of replication and an antibiotic resistance gene to provide for the growth and selection of the expression vector in the bacterial host; a cloning site for insertion of an exogenous DNA sequence; eukaryotic DNA elements that control initiation of transcription of the exogenous gene; and DNA elements that control the processing of transcripts, such as transcription termination/polyadenylation sequences. It also can contain such sequences as are needed for the eventual integration of the vector into the host chromosome.

By "promoter" is meant a regulatory region of DNA capable of regulating the transcription of a sequence linked thereto. It usually comprises a TATA box capable of directing RNA polymerase II to initiate RNA synthesis at the appropriate transcription initiation site for a particular coding sequence. The promoter is the minimal sequence sufficient to direct transcription in a desired manner. The term "regulatory region" is also used to refer to the sequence capable of initiating transcription in a desired manner.

A nucleic acid molecule may be used in conjunction with its own or another promoter. In one embodiment, a selection marker a nucleic acid molecule of interest can be functionally linked to the same promoter. In another embodiment, they can be functionally linked to different promoters. In yet third and fourth embodiments, the expression vector can contain two or more genes of interest that can be linked to the same promoter or different promoters. For example, one promoter can be used to drive a nucleic acid molecule of interest and the selectable marker, or a different promoter used for one or each. These other promoter elements can be those that are constitutive or sufficient to render promoter-dependent gene expression controllable as being cell-type specific, tissue-specific or time or developmental stage specific, or being inducible by external signals or agents. Such elements may be located in the 5' or 3' regions of the gene. Although the additional promoter may be the endogenous promoter of a structural gene of interest, the promoter can also be a foreign regulatory sequence. Promoter elements employed to control expression of product proteins and the selection gene can be any host-compatible promoters. These can be plant gene promoters, such as, for example, the ubiquitin promoter (European patent application no. 0 342 926); the promoter for the small subunit of ribulose-1,5-bisphosphate carboxylase (ssRUBISCO) (Coruzzi et al., 1984; Broglie et al., 1984); or promoters from the tumor-inducing plasmids from *Agrobacterium tumefaciens*, such as the nopaline synthase, octopine synthase and mannopine synthase promoters (Velten and Schell, 1985) that have plant activity; or viral promoters such as the cauliflower mosaic virus (CaMV) 19S and 35S promoters (Guilley et al., 1982; Odell et al., 1985), the figwort mosaic virus FLt promoter (Maiti et al., 1997) or the coat protein promoter of TMV (Grdzelishvili et al., 2000). Alternatively, plant promoters such as heat shock promoters for example soybean hsp 17.5-E (Gurley et al., 1986); or ethanol-inducible promoters (Caddick et al., 1998) may be used. See International Patent Application No. WO 91/19806 for a review of illustrative plant promoters suitably employed.

A promoter can additionally comprise other recognition sequences generally positioned upstream or 5' to the TATA box, referred to as upstream promoter elements, which influence the transcription initiation rate. It is recognized that having identified the nucleotide sequences for a promoter region, it is within the state of the art to isolate and identify further regulatory elements in the 5' region upstream from the particular promoter region identified herein. Thus, the promoter region is generally further defined by comprising upstream regulatory elements such as those responsible for tissue and temporal expression of the coding sequence, enhancers and the like.

Tissue-preferred promoters can be utilized to target enhanced transcription and/or expression within a particular tissue. When referring to preferential expression, what is meant is expression at a higher level in the particular tissue than in other tissue. Examples of these types of promoters include seed preferred expression such as that provided by the phaseolin promoter (Bustos et al. (1989) *The Plant Cell* Vol. 1, 839-853). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa zein, γ-zein, waxy, shrunken 1, shrunken 2, an Ltp1 (See, for example, U.S. Pat. No. 7,550,579), an Ltp2 (Opsahl-Sorteberg, H-G. et al., (2004) *Gene* 341:49-58 and U.S. Pat. No. 5,525,716), and oleosin genes. See also WO 00/12733, where seed-preferred promoters from end1 and end2 genes are disclosed. Seed-preferred promoters also include those promoters that direct gene expression predominantly to specific tissues within the seed such as, for example, the endosperm-preferred promoter of γ-zein, the cryptic promoter from tobacco (Fobert et al. (1994) "T-DNA tagging of a seed coat-specific cryptic promoter in tobacco" *Plant J.* 4: 567-577), the P-gene promoter from corn (Chopra et al. (1996) "Alleles of the maize P gene with distinct tissue specificities encode Myb-homologous proteins with C-terminal replacements" *Plant Cell* 7:1149-1158, Erratum in *Plant Cell* 1997, 1:109), the globulin-1 promoter from corn (Belanger and Kriz (1991) "Molecular basis for Allelic Polymorphism of the maize Globulin-1 gene" *Genetics* 129: 863-972 and GenBank accession No. L22344), promoters that direct expression to the seed coat or hull of corn kernels, for example the pericarp-specific glutamine synthetase promoter (Muhitch et al., (2002) "Isolation of a Promoter Sequence From the Glutamine Synthetase$_{1-2}$ Gene Capable of Conferring Tissue-Specific Gene Expression in Transgenic Maize" *Plant Science* 163:865-872 and GenBank accession number AF359511) and to the embryo (germ) such as that disclosed at U.S. Pat. No. 7,169,967. When referring to a seed or an embryo preferred promoter is meant that it expresses an operably linked sequence to a higher degree in seed or embryo tissue that in other plant tissue. It may express during seed or embryo development, along with expression at other stages, may express strongly during seed or embryo development and to a much lesser degree at other times.

The range of available promoters includes inducible promoters. An inducible regulatory element is one that is capable of directly or indirectly activating transcription of one or more DNA sequences or genes in response to an inducer. In the absence of an inducer the DNA sequences or genes will not be transcribed. Typically, the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. Typically, the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the actin of a pathogen or disease agent such as a virus. A cell containing an inducible regulatory element may be exposed to an inducer by externally applying the inducer to the cell or plant such as by spraying, watering, heating or similar methods.

Any inducible promoter can be used. See Ward et al. *Plant Mol. Biol.* 22: 361-366 (1993). Exemplary inducible promoters include ecdysone receptor promoters, U.S. Pat. No. 6,504,082; promoters from the ACE1 system which responds to copper (Mett et al. *PNAS* 90: 4567-4571 (1993)); In2-1 and In2-2 gene from maize which respond to benzenesulfonamide herbicide safeners (U.S. Pat. No. 5,364,780; Hershey et al., *Mol. Gen. Genetics* 227: 229-237 (1991) and Gatz et al., *Mol. Gen. Genetics* 243: 32-38 (1994)) Tet repressor from Tn10 (Gatz et al., *Mol. Gen. Genet.* 227: 229-237 (1991); or from a steroid hormone gene, the transcriptional activity of which is induced by a glucocorticosteroid hormone. Schena et al., *Proc. Natl. Acad. Sci. U.S.A.* 88: 10421 (1991); the maize GST promoter, which is activated by hydrophobic electrophilic compounds that are used as pre-emergent herbicides; and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991)*Mol. Gen. Genet.* 227:229-237, and U.S. Pat. Nos. 5,814,618 and 5,789,156).

Other components of the vector may be included, also depending upon intended use of the gene. Examples include selectable markers, targeting or regulatory sequences, stabilizing or leader sequences, introns etc. General descriptions and examples of plant expression vectors and reporter genes can be found in Gruber, et al., "Vectors for Plant Transformation" in *Method in Plant Molecular Biology and Biotechnology*, Glick et al eds; CRC Press pp. 89-119 (1993). The selection of an appropriate expression vector will depend upon the host and the method of introducing the expression vector into the host. The expression cassette will also include at the 3' terminus of the heterologous nucleotide sequence of interest, a transcriptional and translational termination region functional in plants.

In one embodiment, the expression vector also contains a gene encoding a selectable or scoreable marker that is operably or functionally linked to a promoter that controls transcription initiation. Examples of selectable markers include those that confer resistance to antimetabolites such as herbicides or antibiotics, for example, dihydrofolate reductase, which confers resistance to methotrexate (Reiss, (1994) *Plant Physiol.* (*Life Sci. Adv.*) 13:143-149; see also Herrera Estrella et al., (1983) *Nature* 303:209-213; Meijer et al., (1991) *Plant Mol. Biol.* 16:807-820); neomycin phosphotransferase, which confers resistance to the aminoglycosides neomycin, kanamycin and paromycin (Herrera-Estrella, (1983) *EMBO J.* 2:987-995, and Fraley et al. (1983) *Proc. Natl. Acad. Sci USA* 80:4803) and hygro, which confers resistance to hygromycin (Marsh, (1984) *Gene* 32:481-485; see also Waldron et al., (1985) *Plant Mol. Biol.* 5:103-108; Zhijian et al., (1995) *Plant Science* 108:219-227); trpB, which allows cells to utilize indole in place of tryptophan; hisD, which allows cells to utilize histinol in place of histidine (Hartman, (1988) *Proc. Natl. Acad. Sci., USA* 85:8047); mannose-6-phosphate isomerase which allows cells to utilize mannose (WO 94/20627); ornithine decarboxylase, which confers resistance to the ornithine decarboxylase inhibitor, 2-(difluoromethyl)-DL-ornithine (DFMO; McConlogue, (1987), in: *Current Communications in Molecular Biology*, Cold Spring Harbor Laboratory ed.); and deaminase from *Aspergillus terreus*, which confers resistance to Blasticidin S (Tamura, (1995) *Biosci. Biotechnol. Biochem.* 59:2336-2338). Additional selectable markers include, for example, a mutant EPSPV-synthase, which confers glyphosate resistance (Hinchee et al., (1998) *BioTechnology* 91:915-922), a mutant acetolactate synthase, which confers imidazolinone or sulfonylurea resistance (Lee et al., (1988) *EMBO J.* 7:1241-1248), a mutant psbA, which confers resistance to atrazine (Smeda et al., (1993) *Plant Physiol.* 103:911-917), or a mutant protoporphyrinogen oxidase (see U.S. Pat. No. 5,767,373), or other markers conferring resistance to an herbicide such as glufosinate. Examples of suitable selectable marker genes include, but are not limited to, genes encoding resistance to chloramphenicol (Herrera Estrella et al., (1983) *EMBO J.* 2:987-992); streptomycin (Jones et al., (1987) *Mol. Gen. Genet.* 210:86-91); spectinomycin (Bretagne-Sagnard et al., (1996) *Transgenic Res.* 5:131-137,); bleomycin (Hille et al., (1990) *Plant Mol. Biol.* 7:171-176,); sulfonamide (Guerineau et al., (1990) *Plant Mol. Biol.* 15:127-136); bromoxynil (Stalker et al., (1988) *Science* (1986) 242:419-423); glyphosate (Shaw et al., *Science* 233:478-481); phosphinothricin (DeBlock et al., (1987) *EMBO J.* 6:2513-2518), and the like. One option for use of a selective gene is a glufosinate-resistance encoding DNA and in one embodiment can be the phosphinothricin acetyl transferase (PAT), maize optimized PAT gene or bar gene under the control of the CaMV 35S or ubiquitin promoters. The genes confer resistance to bialaphos. See, Gordon-Kamm et al., (1990) *Plant Cell* 2:603; Uchimiya et al., (1993) *BioTechnology* 11:835; White et al., *Nucl. Acids Res.* 18:1062, (1990); Spencer et al., 1990) *Theor. Appl. Genet.* 79:625-631, and Anzai et al., (1989) *Mol. Gen. Gen.* 219:492. A version of the PAT gene is the maize optimized PAT gene, described at U.S. Pat. No. 6,096,947.

In addition, markers that facilitate identification of a cell containing the polynucleotide encoding the marker may be employed. Scorable or screenable markers are useful, where presence of the sequence produces a measurable product and can produce the product without destruction of the cell. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase (Jefferson et al. (1987) *The EMBO Journal* vol. 6 No. 13 pp. 3901-3907); alkaline phosphatase. Other screenable markers include the anthocyanin/flavonoid genes in general (See discussion at Taylor and Briggs, (1990) *The Plant Cell* 2:115-127) including, for example, a R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282 (1988)); the genes which control biosynthesis of flavonoid pigments, such as the maize C1 gene (Kao et al., (1996) *Plant Cell* 8: 1171-1179; Scheffler et al. (1994) *Mol. Gen. Genet.* 242:40-48) and maize C2 (Wienand et al., (1986) *Mol. Gen. Genet.* 203:202-207); the B gene (Chandler et al., (1989) *Plant Cell* 1:1175-1183), the p1 gene (Grotewold et al, (1991 *Proc. Natl. Acad. Sci USA*) 88:4587-4591; Grotewold et al., (1994) *Cell* 76:543-553; Sidorenko et al., (1999) *Plant Mol. Biol.* 39:11-19); the bronze locus genes (Ralston et al., (1988) *Genetics* 119:185-197; Nash et al., (1990) *Plant Cell* 2(11): 1039-1049), among others. Yet further examples of suitable markers include the cyan fluorescent protein (CYP) gene (Bolte et al. (2004) *J Cell Science* 117: 943-54 and Kato et al. (2002) *Plant Physiol* 129: 913-42), the yellow fluorescent protein gene (PhiYFP™ from Evrogen; see Bolte et al. (2004) *J. Cell Science* 117: 943-54); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) *EMBO J.* 8:343); a green fluorescent protein (GFP) gene (Sheen et al., (1995) *Plant J.* 8(5):777-84); and DsRed where cells transformed with the marker gene are red in color, and thus visually selectable (Dietrich et al. (2002) *Biotechniques* 2(2):286-293). Additional examples include a p-lactamase gene (Sutcliffe, (1978) *Proc. Nat'l. Acad. Sci. U.S.A.* 75:3737), which encodes an enzyme for which various chromogenic substrates are known (e.g., PADAC, a chromogenic cephalosporin); a xylE gene (Zukowsky et al., (1983) *Proc. Nat'l. Acad. Sci. U.S.A.* 80:1101), which encodes a catechol dioxygenase that can convert chromogenic catechols; an α-amylase gene (Ikuta et al., (1990) *Biotech.* 8:241); and a tyrosinase gene (Katz et al., (1983) *J. Gen. Microbiol.* 129:2703), which encodes an enzyme capable of oxidizing tyrosine to DOPA and dopaquinone, which in turn condenses to form the easily detectable compound melanin. Clearly, many such markers are available to one skilled in the art.

Leader sequences can be included to enhance translation. Various available leader sequences may be substituted or added. Translation leaders are known in the art and include, for example: picornavirus leaders, for example, EMCV leader (encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165 (2):233-8); human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie. (1987) *Nucleic Acids Res.* 15(8):3257-73); and maize chlorotic mottle virus leader (MCMV) (Lommel et al. (1991) *Virology* 81:382-385). See also, Della-Cioppa et al. (1987) *Plant Physiology* 84:965-968.

The expression vector can optionally also contain a signal sequence located between the promoter and the gene of interest and/or after the gene of interest. A signal sequence is a nucleotide sequence, translated to give an amino acid sequence, which is used by a cell to direct the protein or polypeptide of interest to be placed in a particular place within or outside the eukaryotic cell. Many signal sequences are known in the art. See, for example Becker et al., (1992) *Plant Mol. Biol.* 20:49, Knox, C., et al., "Structure and Organization of Two Divergent Alpha-Amylase Genes from Barley", *Plant Mol. Biol.* 9:3-17 (1987), Lerner et al., (1989) *Plant Physiol.* 91:124-129, Fontes et al., (1991) *Plant Cell* 3:483-496, Matsuoka et al., (1991) *Proc. Natl. Acad. Sci.* 88:834, Gould et al., (1989) *J. Cell. Biol.* 108:1657, Creissen et al., (1991) *Plant J.* 2:129, Kalderon, et al., (1984) "A short amino acid sequence able to specify nuclear location," *Cell* 39:499-509, Steifel, et al., (1990) "Expression of a maize cell wall hydroxyproline-rich glycoprotein gene in early leaf and root vascular differentiation" *Plant Cell* 2:785-793. When targeting the protein to the cell wall use of a signal sequence is necessary. One example is the barley alpha-amylase signal sequence. Rogers, J. C. (1985) "Two barley alpha-amylase gene families are regulated differently in aleurone cells" *J. Biol. Chem.* 260: 3731-3738.

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase, *Zea mays* Brittle-1 chloroplast transit peptide (Nelson et al. *Plant Physiol* 117(4):1235-1252 (1998); Sullivan et al. *Plant Cell* 3(12):1337-48; Sullivan et al., *Planta* (1995) 196(3):477-84; Sullivan et al., *J. Biol. Chem.* (1992) 267 (26):18999-9004) and the like. One skilled in the art will readily appreciate the many options available in expressing a product to a particular organelle. Use of transit peptides is well known (e.g., see U.S. Pat. Nos. 5,717,084; 5,728,925). A protein may be targeted to the endoplasmic reticulum of the plant cell. This may be accomplished by use of a localization sequence, such as KDEL. This sequence (Lys-Asp-Glu-Leu) contains the binding site for a receptor in the endoplasmic reticulum. (Munro et al., (1987) "A C-terminal signal prevents secretion of luminal ER proteins." *Cell.* 48:899-907. Retaining the protein in the vacuole is another example. Signal sequences to accomplish this are well known. For example, Raikhel U.S. Pat. No. 5,360,726 shows a vacuole signal sequence as does Warren et al at U.S. Pat. No. 5,889,174. Vacuolar targeting signals may be present either at the amino-terminal portion, (Holwerda et al., (1992) *The Plant Cell*, 4:307-318, Nakamura et al., (1993) *Plant Physiol.*, 101:1-5), carboxy-terminal portion, or in the internal sequence of the targeted protein. (Tague et al., (1992) *The Plant Cell*, 4:307-318, Saalbach et al. (1991) *The Plant Cell*, 3:695-708). Additionally, amino-terminal sequences in conjunction with carboxy-terminal sequences are responsible for vacuolar targeting of gene products (Shinshi et al. (1990) *Plant Molec. Biol.* 14:357-368).

In addition to a promoter, the expression cassette can include one or more enhancers. By "enhancer" is intended a cis-acting sequence that increases the utilization of a promoter. Such enhancers can be native to a gene or from a heterologous gene. Further, it is recognized that some promoters can contain one or more enhancers or enhancer-like elements. An example of one such enhancer is the 35S enhancer, which can be a single enhancer, or duplicated. See for example, McPherson et al, U.S. Pat. No. 5,322,938. Other methods known to enhance translation can also be utilized, for example, introns, and the like. Other modifications can improve expression, include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The termination region can be native with the promoter nucleotide sequence can be native with the DNA sequence of interest, or can be derived from another source. Convenient termination regions are available from the Ti-plasmid of *A, tumefaciens*, such as the octopine synthase (MacDonald et al., (1991) *Nuc. Acids Res.* 19(20)5575-5581) and nopaline synthase termination regions (Depicker et al., (1982) *Mol. and Appl. Genet.* 1:561-573 and Shaw et al. (1984) *Nucleic Acids Research* Vol. 12, No. 20 pp 7831-7846 (nos)). Examples of various other terminators include the pin II terminator from the protease inhibitor II gene from potato (An, et al. (1989) *Plant Cell* 1, 115-122. See also, Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Many variations on the promoters, selectable markers, signal sequences, leader sequences, termination sequences, introns, enhancers and other components of the vector are available to one skilled in the art.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions, such as transitions and transversions, can be involved.

The transformation vector comprising the sequence operably linked to a heterologous nucleotide sequence in an expression cassette, can also contain at least one additional nucleotide sequence for a gene to be cotransformed into the organism. Alternatively, the additional sequence(s) can be provided on another transformation vector.

The method of transformation/transfection is not critical; various methods of transformation or transfection are currently available. As newer methods are available to transform crops or other host cells they may be directly applied. Accordingly, a wide variety of methods have been developed to insert a DNA sequence into the genome of a host cell to obtain the transcription or transcript and translation of the sequence to effect phenotypic changes in the organism. Thus, any method which provides for efficient transformation/transfection may be employed.

Methods for introducing expression vectors into plant tissue available to one skilled in the art are varied and will depend on the plant selected. Procedures for transforming a wide variety of plant species are well known and described throughout the literature. (See, for example, Miki and McHugh (2004) *Biotechnol.* 107, 193-232; Klein et al. (1992) *Biotechnology* (NY) 10, 286-291; and Weising et al. (1988) *Annu. Rev. Genet.* 22, 421-477). For example, the DNA construct may be introduced into the genomic DNA of the plant cell using techniques such as microprojectile-mediated delivery (Klein et al. 1992, supra), electroporation (Fromm et al., 1985 *Proc. Natl. Acad. Sci. USA* 82, 5824-5828), polyethylene glycol (PEG) precipitation (Mathur and Koncz, 1998 *Methods Mol. Biol.* 82, 267-276), direct gene transfer (WO 85/01856 and EP-A-275 069), in vitro protoplast transformation (U.S. Pat. No. 4,684,611), and microinjection of plant cell protoplasts or embryogenic callus (Crossway, A. (1985) *Mol. Gen. Genet.* 202, 179-185). *Agrobacterium* transformation methods of Ishida et al. (1996) and also described in U.S. Pat. No. 5,591,616 are yet another option. Co-cultivation of plant tissue with *Agrobacterium tumefaciens* is a variation, where the DNA constructs are placed into a binary vector system (Ishida et al., 1996 *Nat. Biotechnol.* 14, 745-750). The virulence functions of the *Agrobacterium tumefaciens* host will direct the insertion of the construct into the plant cell DNA when the cell is infected by the bacteria. See, for example, Fraley et al. (1983) *Proc. Natl. Acad. Sci. USA,* 80, 4803-4807. *Agrobacterium* is primarily used in dicots, but monocots including maize can be transformed by *Agrobacterium*. See, for example, U.S. Pat. No. 5,550,318. In one of many variations on the method, *Agrobacterium* infection of corn can be used with heat shocking of immature embryos (Wilson et al. U.S. Pat. No. 6,420,630) or with antibiotic selection of Type II callus (Wilson et al., U.S. Pat. No. 6,919,494).

Rice transformation is described by Hiei et al. (1994) *Plant J.* 6, 271-282 and Lee et al. (1991) *Proc. Nat. Acad. Sci. USA* 88, 6389-6393. Standard methods for transformation of canola are described by Moloney et al. (1989) *Plant Cell Reports* 8, 238-242. Corn transformation is described by Fromm et al. (1990) *Biotechnology* (NY) 8, 833-839 and Gordon-Kamm et al. (1990) supra. Wheat can be transformed by techniques similar to those used for transforming corn or rice. Sorghum transformation is described by Casas et al. (Casas et al. (1993) Transgenic sorghum plants via microprojectile bombardment. *Proc. Natl. Acad. Sci. USA* 90, 11212-11216) and barley transformation is described by Wan and Lemaux (Wan and Lemaux (1994) Generation of large numbers of independently transformed fertile barley plants. *Plant Physiol.* 104, 37-48). Soybean transformation is described in a number of publications, including U.S. Pat. No. 5,015,580.

In one method, the *Agrobacterium* transformation methods of Ishida et al. (1996) and also described in U.S. Pat. No. 5,591,616, are generally followed, with modifications that the inventors have found improve the number of transformants obtained. The Ishida method uses the A188 variety of maize that produces Type I callus in culture. In an embodiment the Hi II maize line is used which initiates Type II embryogenic callus in culture (Armstrong et al., 1991).

While Ishida recommends selection on phosphinothricin when using the bar or pat gene for selection, another preferred embodiment provides use of bialaphos instead. In general, as set forth in the U.S. Pat. No. 5,591,616 patent, and as outlined in more detail below, dedifferentiation is obtained by culturing an explant of the plant on a dedifferentiation-inducing medium for not less than seven days, and the tissue during or after dedifferentiation is contacted with *Agrobacterium* having the gene of interest. The cultured tissue can be callus, an adventitious embryo-like tissue or suspension cells, for example. In this preferred embodiment, the suspension of *Agrobacterium* has a cell population of $10^6$ to $10^{11}$ cells/ml and are contacted for three to ten minutes with the tissue, or continuously cultured with *Agrobacterium* for not less than seven days. The *Agrobacterium* can contain plasmid pTOK162, with the gene of interest between border sequences of the T region of the plasmid, or the gene of interest may be present in another plasmid-containing *Agrobacterium*. The virulence region may originate from the virulence region of a Ti plasmid or Ri plasmid. The bacterial strain used in the Ishida protocol is LBA4404 with the 40 kb super binary plasmid containing three vir loci from the hypervirulent A281 strain. The plasmid has resistance to tetracycline. The cloning vector cointegrates with the super binary plasmid. Since the cloning vector has an *E. coli* specific replication origin, but not an *Agrobacterium* replication origin, it cannot survive in *Agrobacterium* without cointegrating with the super binary plasmid. Since the LBA4404 strain is not highly virulent, and has limited application without the super binary plasmid, the inventors have found in yet another embodiment that the EHA101 strain is preferred. It is a disarmed helper strain derived from the hypervirulent A281 strain. The cointegrated super binary/cloning vector from the LBA4404 parent is isolated and electroporated into EHA101, selecting for spectinomycin resistance. The plasmid is isolated to assure that the EHA101 contains the plasmid. EHA101 contains a disarmed pTi that carries resistance to kanamycin. See, Hood et al. (1986).

Further, the Ishida protocol as described provides for growing fresh culture of the *Agrobacterium* on plates, scraping the bacteria from the plates, and resuspending in the co-culture medium as stated in the U.S. Pat. No. 5,591,616 patent for incubation with the maize embryos. This medium includes 4.3 g MS salts, 0.5 mg nicotinic acid, 0.5 mg pyridoxine hydrochloride, 1.0 ml thiamine hydrochloride, casamino acids, 1.5 mg 2,4-D, 68.5 g sucrose and 36 g glucose per liter, all at a pH of 5.8. In a further preferred method, the bacteria are grown overnight in a 1 ml culture and then a fresh 10 ml culture is re-inoculated the next day when transformation is to occur. The bacteria grow into log phase, and are harvested at a density of no more than $OD_{600}$=0.5, preferably between 0.2 and 0.5. The bacteria are then centrifuged to remove the media and resuspended in the co-culture medium. Since Hi II is used, medium preferred for Hi II is used. This medium is described in considerable detail by Armstrong and Green (1985). The resuspension medium is the same as that described above. All further Hi II media are as described in Armstrong and Green (1985). The result is redifferentiation of the plant cells and regeneration into a plant. Redifferentiation is sometimes referred to as dedifferentiation, but the former term more accurately describes the process where the cell begins with a form and identity, is placed on a medium in which it loses that identity, and becomes "reprogrammed" to have a new identity. Thus, the scutellum cells become embryogenic callus.

A transgenic plant may be produced that contains an introduced nucleic acid molecule encoding the Ag2.

When referring to introduction of a nucleotide sequence into a plant is meant to include transformation into the cell, as well as crossing a plant having the sequence with another plant, so that the second plant contains the heterologous sequence, as in conventional plant breeding techniques. Such breeding techniques are well known to one skilled in the art. This can be accomplished by any means known in the art for breeding plants such as, for example, cross pollination of the transgenic plants that are described above with other plants, and selection for plants from subsequent generations which express the amino acid sequence. The plant breeding methods used herein are well known to one skilled in the art. For a discussion of plant breeding techniques, see Poehlman (1995) *Breeding Field Crops*. AVI Publication Co., Westport Conn., 4th Edit.). Many crop plants useful in this method are bred through techniques that take advantage of the plant's method of pollination. A plant is self-pollinating if pollen from one flower is transferred to the same or another flower of the same plant. A plant is cross-pollinating if the pollen comes from a flower on a different plant. For example, in *Brassica*, the plant is normally self-sterile and can only be cross-pollinated unless, through discovery of a mutant or through genetic intervention, self-compatibility is obtained. In self-pollinating species, such as rice, oats, wheat, barley, peas, beans, soybeans, tobacco and cotton, the male and female plants are anatomically juxtaposed. During natural pollination, the male reproductive organs of a given flower pollinate the female reproductive organs of the same flower. Maize plants (*Zea mays* L.) can be bred by both self-pollination and cross-pollination techniques. Maize has male flowers, located on the tassel, and female flowers, located on the ear, on the same plant. It can self or cross-pollinate.

Pollination can be by any means, including but not limited to hand, wind or insect pollination, or mechanical contact between the male fertile and male sterile plant. For production of hybrid seeds on a commercial scale in most plant species pollination by wind or by insects is preferred. Stricter control of the pollination process can be achieved by using a variety of methods to make one plant pool male sterile, and the other the male fertile pollen donor. This can be accomplished by hand detassling, cytoplasmic male sterility, or control of male sterility through a variety of methods well known to the skilled breeder. Examples of more sophisticated male sterility systems include those described by Brar et al., U.S. Pat. Nos. 4,654,465 and 4,727,219 and Albertsen et al., U U.S. Pat. Nos. 5,859,341 and 6,013,859.

Backcrossing methods may be used to introduce the gene into the plants. This technique has been used for decades to introduce traits into a plant. An example of a description of this and other plant breeding methodologies that are well known can be found in references such as Neal (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

Any plant species may be used, whether monocotyledonous or dicotyledonous, including but not limited to corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), oats (*Avena*), barley (*Hordeum*), vegetables, ornamentals, and conifers. Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.) and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and *chrysanthemum*. Conifers which may be employed in practicing the present invention include, for example, pines such as loblolly pine (*Pinus taeda*), slash pine (*Pinus elliotii*), ponderosa pine (*Pinus ponderosa*), lodgepole pine (*Pinus contotta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Selection and propagation techniques described above yield a plurality of transgenic plants that are harvested in a conventional manner. The plant or any parts expressing the recombinant polypeptide can be used in a commercial process, or the polypeptide extracted. When using the plant or part itself, it can, for example, be made into flour and then applied in the commercial process. Polypeptide extraction from biomass can be accomplished by known methods. Downstream processing for any production system refers to all unit operations after product synthesis, in this case protein production in transgenic seed (Kusnadi, A. R., Nikolov, Z. L., Howard, J. A., 1997. *Biotechnology and Bioengineering*. 56:473-484). For example, seed can be processed either as whole seed ground into flour or fractionated and the germ separated from the hulls and endosperm. If germ is used, it is usually defatted using an extraction process and the remaining crushed germ ground into a meal or flour. In some cases, the germ is used directly in the process or the protein can be extracted (See, e.g. WO 98/39461). Extraction is generally made into aqueous buffers at specific pH to enhance recombinant protein extraction and minimize native seed protein extraction. Subsequent protein concentration or purification can follow.

The compositions and process described here are also to producing and administering a vaccine that protects an animal from Valley Fever. When referring to the condition of Valley Fever is meant to include a person infected by *Coccidioides* and that may (or may not) have any of the symptoms described here. These conditions can include common coccidiodomycosis and those Valley Fever symptoms of chronic coccidiodomycosis and disseminated coccidiodomycosis (examples of such symptoms describe later herein).

The vaccine may be administered to any animal. Some animals may be infected and yet not show symptoms, but can be vaccinated to prevent spread of the fungus. By way of example without limitation, animals susceptible to infection by *Coccidioides* include dogs, cats, cattle, pigs and other livestock, horses, llamas and alpacas, apes and monkeys, zoo animals such as kangaroos, wallabies, tigers, bears, badgers, otters, marine animals such as sea otters, dolphins and sea lions.

As used herein, the term "vaccine" as used herein refers to a pharmaceutical composition comprising at least one protective molecule, that induces protective response in an animal and possibly, but not necessarily, one or more additional components that enhance the activity of said active component. A vaccine may additionally comprise further components typical to pharmaceutical compositions. In another form, the immunologically active component of a vaccine may comprise appropriate elements of said organisms (subunit vaccines) whereby these elements are generated by any variety of methods such as by destroying the whole organism or the growth cultures of such microorganisms and subsequent purification steps yielding in the desired structure(s), by isolation from samples, or by synthetic processes induced by an appropriate manipulation of a suitable system such as, but not restricted to, bacteria, insects, mammalian, or other species, plus subsequent isolation and purification procedures or by induction of said synthetic processes in the animal needing a vaccine by direct incorporation of genetic material using suitable pharmaceutical compositions (polynucleotide vaccination). A vaccine may comprise one or simultaneously more than one of the elements described above.

It is possible to provide an adjuvant in the vaccine. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses. Immunostimulatory agents or adjuvants have been used for many years to improve the host immune responses to, for example, vaccines. The vaccines of the present invention may be used in conjunction with an adjuvants, for example, lipopolysaccharides, aluminum hydroxide and aluminum phosphate (alum), saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes. Desirable characteristics of ideal adjuvants may include: (1) lack of toxicity; (2) ability to stimulate a long-lasting immune response; (3) simplicity of manufacture and stability in long-term storage; (4) ability to elicit both CMI and HIR to antigens administered by various routes; (5) synergy with other adjuvants; (6) capability of selectively interacting with populations of antigen presenting cells (APC); (7) ability to specifically elicit appropriate T-cell helper 1 (TH 1) or TH 2 cell-specific immune responses; and (8) ability to selectively increase appropriate antibody isotype levels (for example, IgA) against antigens. An adjuvant used with the present compositions and methods need not possess all these characteristics to be used.

The terms "protecting", "protection", "protective immunity" or "protective immune response," as used herein, are intended to mean that the fungal load on the animal is reduced, or the host animal mounts an active immune response to the vaccine or polypeptides of the present invention, such that upon exposure to disease challenge, the animal is able to combat the infection. The fungal load is reduced when the amount of fungus present in the animal is decreased. Thus, a protective immune response will decrease the incidence of morbidity and mortality from exposure to the microorganism among a host animal. The animal will be protected from subsequent exposure to the disease-causing agent. In an embodiment, the animal may be protected by treating the animal which has already been exposed to the disease-causing agent by administration of the vaccine or polypeptide after such exposure. In such an instance there is also shown to be a lessening of morbidity and mortality. Those skilled in the art will understand that in a commercial animal setting, the production of a protective immune response may be assessed by evaluating the effects of vaccination on the group or herd as a whole, e.g., there may still be morbidity and mortality in a minority of vaccinated animals. Furthermore, protection also includes a lessening in severity of any gross or histopathological changes and/or of symptoms of the disease, as compared to those changes or symptoms typically caused by the isolate in similar animals which are unprotected (i.e., relative to an appropriate control). Thus, a protective immune response will decrease the symptoms of the disease, which will vary. They may include, for example, fever, chest pain, coughing, chills, night sweats, headache, fatigue, joint aches and/or a red spotty rash. Chronic coccidioidomycosis (Valley Fever) can include low-grade fever, weight loss, cough, check pain, blood-tinged sputum and/or nodules in the lungs. A serious form of the disease is disseminated coccidioidomycosis which occurs when the infection spreads to other parts of the body beyond the lungs. It may for example disseminate to the skin, bones, liver, brain, hears and meninges. Symptoms in this instance include nodules, ulcers and skin lesions, painful lesions in the skull, spin or other bones, painful, swollen joints and meningitis. In certain instances, the animal may not necessarily produce antibodies that can be measured, yet disease morbidity and/or mortality is reduced and where there also may be a reduced titer of infection upon exposure to the microorganism.

As used herein, "immunogenically effective amount" refers to an amount, which is effective in reducing, eliminating, treating, preventing or controlling the symptoms of the infections, diseases, disorders, or condition.

Vaccines are "administered" in an embodiment of the methods by oral delivery, and also by non-oral delivery. Non-oral delivery may be, for example, parenteral, injection subcutaneously or intramuscularly, into an organ or cavity of the animal; may be by transdermal or by gas exchange. Other examples of non-oral delivery includes, but is not limited to, syringes, nebulizers, misters, needleless injection devices, or microprojectile bombardment gene guns (biolistic bombardment), via a liposome delivery system, naked delivery system, electroporation, viruses, vectors, viral vectors, The immunogenic preparations and vaccines are administered in a manner compatible with the dosage formulation, and in such amount as will be therapeutically effective, immunogenic and protective.

The quantity to be administered depends on the subject to be treated, including, for example, the capacity of the immune system of the individual to mount a protective response. In an embodiment the present methods provide for an initial dose of oral and/or non-oral administration of the vaccine. Another embodiment provides for a second such administration of both oral and/or non-oral delivery. In one embodiment the oral and non-oral administration occurs within three days of the other. The result is a protective response which includes an increased immune response compared to either parental alone or oral alone, and reduces the number of administrations of the vaccine necessary. The present method can be included with other boosting regimes if desired.

With the present methods, the animal receives one or more doses, and may receive two, three, four, five, six, seven, eight, nine, ten or more doses. Doses of the plant-produced vaccine may be administered in addition to one or more doses of a non-plant produced vaccine before, after or at the same time as the plant-produced vaccine. Delivery may be oral or non-oral, such as injected. In an embodiment, the animal receives two or more doses, that is, one delivery of the vaccine that provides a protective response via non-oral such as injection and also receives a second delivery of the vaccine providing protective response to those same diseases via oral delivery. The oral vaccine may be delivered first or second or at the same time as the non-oral administration.

The following is provided by way of example and is not intended to limit the scope of the invention. All references cited herein are incorporated herein by reference.

EXAMPLES

Example 1

As mentioned above, production of Ag2 has been extremely low in microbes prohibiting production at a cost compatible for commercialization. Typically, yields of grams/liter are obtained for most recombinant protein products from microbes. In this case, Ag2 is at levels >100-fold lower which led us to investigate alternative hosts. Plant-produced proteins have shown great promise in that they can accumulate recombinant proteins at much higher levels than microbes for some recalcitrant proteins and are the least expensive source of proteins in general[20-22] Not all plant systems however, are created equal. There is a wide variation in the cost, scalability, agents that interfere with purification such as proteases, lignin and phenols, storage properties and, safety with regard to allergenic, carcinogenic or toxin material in the host. These characteristics have been reviewed elsewhere[21] and maize has emerged as one of the premier systems leading to recent commercialization of several recombinant proteins.

This is particularly true for the high accumulation of vaccine candidates. For example, reports of the accumulation of hepatitis B surface antigen (HBsAg) in edible plant tissue (other than maize) have varied dramatically with banana fruit being one of the lowest at 0.001 µg/gram fresh weight and potato being one of the highest at 8 µg/gram fresh weight[23, 24]. In our maize-based system, HBsAg has been expressed at >200 µg/g.

This high level of antigen in the grain leads to a cost of the raw material below $0.01/dose even when accumulation is only 10 µg/g. However, purification costs can account for 90% of the product and is inversely proportional to the concentration in the biomass. Cost models have shown that levels as low as 10 µg/g may be economically feasible but for most cases levels of 100 mg/kg are targeted to keep purification costs low. This level is approximately 10-fold higher than what has been achieved in microbes. Therefore, on embarking on accumulating Ag2 in maize, several approaches to accumulate high levels were employed and are described below.

Development of an Ag2 Specific ELISA.

To analyze for Ag2 in grain, an ELISA was developed. The strategy was to develop a sandwich ELISA. This requires antibodies to Ag2 that are not commercially available; therefore, the first step was to make antibodies. In order to make the antibodies we needed to have a supply of Ag2. Therefore Ag2 was made from bacterial cultures using a histidine tag fused to the Ag2 protein and fused to thrombin with a thrombin cleavage site as described previously[17]. The protein was purified as described previously over a nickel column and the protein was compared to a previously purified standard using gel electrophoresis. This protein was then used to immunize rabbits and make polyclonal antibodies. The rabbit antibodies were tested for their ability to detect Ag2 by Western blot analysis. A portion of the antibodies was then purified on a protein A column followed by biotinylation using a commercially available kit (Sigma Chemical Company. St. Louis, Mo.).

Using the purified Ag2 as a standard, sera from Ag2 injected rabbits as the capture antibody, the biotinylated antibody as the detection antibody and alkaline phosphatase fused to streptavidin, the sandwich ELISA was optimized for concentrations of the various reagents. An example of the results is shown in FIG. 1 where the detection limit for the Ag2 is below 1 ng.

After selecting the optimal concentrations for each of the reagents, purified Ag2 from the bacterial culture was spiked into various concentrations of seed extracts to ensure there was no significant interference (data not shown). Although the assay is not validated at this stage of development, it can be used to give a first approximation of the accumulation of the Ag2 in tissues and discern between high and low expressing lines.

Extraction of Ag2 from Maize Grain.

It is known that Ag2 has poor solubility in standard aqueous buffers such as PBS. Therefore, various detergents were employed to extract the protein from maize grain. Grain from plants that contained the expression construct VFE was used to test the various treatments.

While several of the treatments below showed a strong signal to noise ratio at one given concentration, they were not proportional when diluted making it difficult to quantify When PBS that contained 1% Triton X-100 a strong signal to noise ratio was observed at a dilution of 1:250 of the seed extract and this was proportional to at least a 1:1000 dilution.

Therefore, this treatment was used for all subsequent extractions. While further optimization and validation are required for this assay, these conditions can provide relative levels of Ag2 in the different constructs and between individual events.

REFERENCES

[1] Chabot, I., Goetghebeur, M. M., and Grégoire, J.-P. (2004) The societal value of universal childhood vaccination, *Vaccine* 22, 1992-2005.

[2] Hilleman, M. R. (2000) Vaccines in historic evolution and perspective: a narrative of vaccine discoveries, *Vaccine* 18, 1436-1447.

[3] Wilson, L. S., Reyes, C. M., Stolpman, M., Speckman, J., Allen, K., and Beney, J. (2002) The direct cost and incidence of systemic fungal infections, *Value in Health* 5, 26-34.

[4] Tarcha, E. J., Basrur, V., Hung, C.-Y., Gardner, M. J., and Cole, G. T. (2006) Multivalent recombinant protein vaccine against coccidioidomycosis, *Infection and Immunity* 74, 5802-5813.

[5] Smith, C. E., and Beard, R. R. (1946) Varieties of Coccidioidal Infection in Relation to the Epidemiology and Control of the Diseases, *American Journal of Public Health and the Nations Health* 36, 1394-1402.

[6] Nguyen, C., Barker, B. M., Hoover, S., Nix, D. E., Ampel, N. M., Frelinger, J. A., Orbach, M. J., and Galgiani, J. N. (2013) Recent advances in our understanding of the environmental, epidemiological, immunological, and clinical dimensions of coccidioidomycosis, *Clinical Microbiology Reviews* 26, 505-525.

[7] Pappagianis, D. (2001) Seeking a Vaccine against *Coccidioides immitis* and Serologic Studies: Expectations and Realities, *Fungal Genetics and Biology* 32, 1-9.

[8] Borchers, A. T., and Gershwin, M. E. (2010) The immune response in *Coccidioidomycosis, Autoimmunity Reviews* 10, 94-102.

[9] Fisher, B. T., Chiller, T. M., Prasad, P. A., Beveridge, M., Walsh, T. J., and Zaoutis, T. E. (2010) Hospitalizations for coccidioidomycosis at forty-one children's hospitals in the United States, *The Pediatric Infectious Disease Journal* 29, 243-247.

[10] CDC. (2013) Increase in reported coccidioidomycosis—United States, 1998-2011, *Morbidity and Mortality Weekly Report* 62, 217-221.

[11] Cole, G. T., Hung, C.-Y., Sanderson, S. D., Hurtgen, B. J., Wüthrich, M., Klein, B. S., Deepe, G. S., Ostroff, G. R., and Levitz, S. M. (2013) Novel strategies to enhance vaccine immunity against coccidioidomycosis, *PLoS pathogens* 9, e1003768.

[12] USCensusBureau. (2014) State and County Quick-Facts.

[13] AZ-ToursimOffice. (2014) Arizona Travel Industry Performance, 2014.

[14] VisitCalifornia. (2014) International Travel to California.

[15] Las_Vegas_Conventions_and_Visitors_Authority. (2014) Vegas FAQs.

[16] Delgado, N., Xue, J., Yu, J.-J., Hung, C.-Y., and Cole, G. T. (2003) A recombinant β-1, 3-glucanosyltransferase homolog of *Coccidioides posadasii* protects mice against coccidioidomycosis, *Infection and Immunity* 71, 3010-3019.

[17] Herr, R. A., Hung, C.-Y., and Cole, G. T. (2007) Evaluation of two homologous proline-rich proteins of *Coccidioides posadasii* as candidate vaccines against coccidioidomycosis, *Infect Immun* 75, 5777-5787.

[18] Hurtgen, B. J., Hung, C.-Y., Ostroff, G. R., Levitz, S. M., and Cole, G. T. (2012) Construction and evaluation of a novel recombinant T cell epitope-based vaccine against coccidioidomycosis, *Infect Immun* 80, 3960-3974.

[19] Shubitz, L. F., Yu, J.-J., Hung, C.-Y., Kirkland, T. N., Peng, T., Perrill, R., Simons, J., Xue, J., Herr, R. A., and Cole, G. T. (2006) Improved protection of mice against lethal respiratory infection with *Coccidioides posadasii* using two recombinant antigens expressed as a single protein, *Vaccine* 24, 5904-5911.

[20] Howard, J. A., and Hood, E. E. (2007) Methods for Growing Nonfood Products in Transgenic Plants, *Crop science* 47, 1255-1262.

[21] Howard, J. A., and Hood, E. (2005) Bioindustrial and biopharmaceutical products produced in plants, In *Advances in Agronomy* (Sparks, D., Ed.), pp 91-124, Academic Press.

[22] Howard, J. A. (2005) Commercialization of biopharmaceutical and bioindustrial proteins from plants, *Crop Science* 45, 468-472.

[23] Kumar, G., Ganapathi, T., and Bapat, V. (2007) Production of hepatitis B surface antigen in recombinant plant systems: an update, *Biotechnology progress* 23, 532-539.

[24] Hayden, C. A. (2014) An oral vaccine for hepatitis B: challenges, setbacks, and breakthroughs, In *Commercial Plant-Produced Recombinant Protein Products*, pp 197-228, Springer.

[25] Streatfield, S. J. (2006) Mucosal immunization using recombinant plant-based oral vaccines, *Methods* 38, 150-157.

[26] Egelkrout, E., Raj an, V., and Howard, J. A. (2012) Overproduction of recombinant proteins in plants, *Plant science* 184, 83-101.

[27] Soria-Guerra, R. E., Moreno-Fierros, L., and Rosales-Mendoza, S. (2011) Two decades of plant-based candidate vaccines: a review of the chimeric protein approaches, *Plant cell reports* 30, 1367-1382.

[28] Rosales-Mendoza, S., Alpuche-Solís, Á. G., Soria-Guerra, R. E., Moreno-Fierros, L., Martínez-González, L., Herrera-Díaz, A., and Korban, S. S. (2009) Expression of an *Escherichia coli* antigenic fusion protein comprising the heat labile toxin B subunit and the heat stable toxin, and its assembly as a functional oligomer in transplastomic tobacco plants, *The Plant Journal* 57, 45-54.

[29] Mohamadzadeh, M., Duong, T., Sandwick, S. J., Hoover, T., and Klaenhammer, T. R. (2009) Dendritic cell targeting of *Bacillus anthracis* protective antigen expressed by *Lactobacillus acidophilus* protects mice from lethal challenge, *Proc Natl Acad Sci USA* 106, 4331-4336.

[30] Hayden, C. A., Streatfield, S. J., Lamphear, B. J., Fake, G. M., Keener, T. K., Walker, J. H., Clements, J. D., Turner, D. D., Tizard, I. R., and Howard, J. A. (2012) Bioencapsulation of the hepatitis B surface antigen and its use as an effective oral immunogen, *Vaccine* 30, 2937-2942.

[31] Wüthrich, M., Gem, B., Hung, C. Y., Ersland, K., Rocco, N., Pick-Jacobs, J., Galles, K., Filutowicz, H., Warner, T., and Evans, M. (2011) Vaccine-induced protection against 3 systemic mycoses endemic to North America requires Th17 cells in mice, *The Journal of clinical investigation* 121, 554-568.

[32] Hung, C.-Y., Gonzalez, A., Wüthrich, M., Klein, B. S., and Cole, G. T. (2011) Vaccine immunity to coccidioidomycosis occurs by early activation of three signal pathways of T helper cell response (Th1, Th2, and Th17), *Infect Immun* 79, 4511-4522.

[33] Soto, E. R., Caras, A. C., Kut, L. C., Castle, M. K., and Ostroff, G. R. (2012) Glucan particles for macrophage targeted delivery of nanoparticles, *Journal of drug delivery* 2012.

[34] De Smet, R., Demoor, T., Verschuere, S., Dullaers, M., Ostroff, G. R., Leclercq, G., Allais, L., Pilette, C., Dierendonck, M., and De Geest, B. G. (2013) β-Glucan microparticles are good candidates for mucosal antigen delivery in oral vaccination, *Journal of controlled release* 172, 671-678.

[35] De Jesus, M., Ostroff, G. R., Levitz, S. M., Bartling, T. R., and Mantis, N. J. (2014) A population of Langerin-positive dendritic cells in murine Peyer's patches involved in sampling β-glucan microparticles, *PLoS One* 9, e91002.

[36] Tipper, D. J., and Szomolanyi-Tsuda, E. (2016) Scaffolded Antigens in Yeast Cell Particle Vaccines Provide Protection against Systemic Polyoma Virus Infection, *Journal of immunology research* 2016.

[37] Tacket, C. O., Pasetti, M. F., Edelman, R., Howard, J. A., and Streatfield, S. (2004) Immunogenicity of recombinant LT-B delivered orally to humans in transgenic corn, *Vaccine* 22, 4385-4389.

[38] Lamphear, B. J., Streatfield, S. J., Jilka, J. M., Brooks, C. A., Barker, D. K., Turner, D. D., Delaney, D. E., Garcia, M., Wiggins, B., and Woodard, S. L. (2002) Delivery of subunit vaccines in maize seed, *Journal of Controlled Release* 85, 169-180.

[39] Lamphear, B. J., Jilka, J. M., Kesl, L., Welter, M., Howard, J. A., and Streatfield, S. J. (2004) A corn-based delivery system for animal vaccines: an oral transmissible gastroenteritis virus vaccine boosts lactogenic immunity in swine, *Vaccine* 22, 2420-2424.

[40] Mirza, Z., Soto, E. R., Dikengil, F., Levitz, S. M., and Ostroff, G. R. (2017) Beta-Glucan Particles as Vaccine Adjuvant Carriers, *Vaccines for Invasive Fungal Infections: Methods and Protocols,* 143-157.

[41] Young, S. H., Ostroff, G. R., Zeidler-Erdely, P. C., Roberts, J. R., Antonini, J. M., and Castranova, V. (2007) A comparison of the pulmonary inflammatory potential of different components of yeast cell wall, *Journal of toxicology and environmental health. Part A* 70, 1116-1124.

[42] Hurtgen, B. J., Hung, C. Y., Ostroff, G. R., Levitz, S. M., and Cole, G. T. (2012) Construction and evaluation of a novel recombinant T cell epitope-based vaccine against coccidioidomycosis, *Infection and immunity* 80, 3960-3974.

[43] Hayden, C. A., Smith, E. M., Turner, D. D., Keener, T. K., Wong, J. C., Walker, J. H., Tizard, I. R., Jimenez-Flores, R., and Howard, J. A. (2014) Supercritical fluid extraction provides an enhancement to the immune response for orally-delivered hepatitis B surface antigen, *Vaccine* 32, 1240-1246.

[44] Van der Lubben, I., Verhoef, J., Borchard, G., and Junginger, H. (2001) Chitosan for mucosal vaccination, *Advanced drug delivery reviews* 52, 139-144.

[45] Lamphear, B. J., Streatfield, S. J., Jilka, J. M., Brooks, C. A., Barker, D. K., Turner, D. D., Delaney, D. E., Garcia, M., Wiggins, B., Woodard, S. L., Hood, E. E., Tizard, I. R., Lawhorn, B., and Howard, J. A. (2002) Delivery of subunit vaccines in maize seed, *J Control Release* 85, 169-180.

[46] Streatfield, S. J., Lane, J. R., Brooks, C. A., Barker, D. K., Poage, M. L., Mayor, J. M., Lamphear, B. J., Drees, C. F., Jilka, J. M., Hood, E. E., and Howard, J. A. (2003) Corn as a production system for human and animal vaccines, *Vaccine* 21, 812-815.

Example 2

Materials and Methods
Construct Design

Sequences utilized in the experiments below are as follows. Reference to the promoter pr25 refers to the maize globulin-1 gene (SEQ ID NO: 12), pr39 refers to a maize 27 kD gamma-zein gene, (SEQ ID NO: 13); and pr44 refers to the pr25 globulin-1 promoter, with two extra copies of a portion of the promoter (SEQ ID NO: 14). In the examples the following sequences were used in the experiments: cell wall signal sequence (BAASS) (SEQ ID NO: 15); vacuole signal sequence (SEQ ID NO: 16); endoplasmic reticulum signal sequence (SEQ ID NO: 17).

Figure 2:
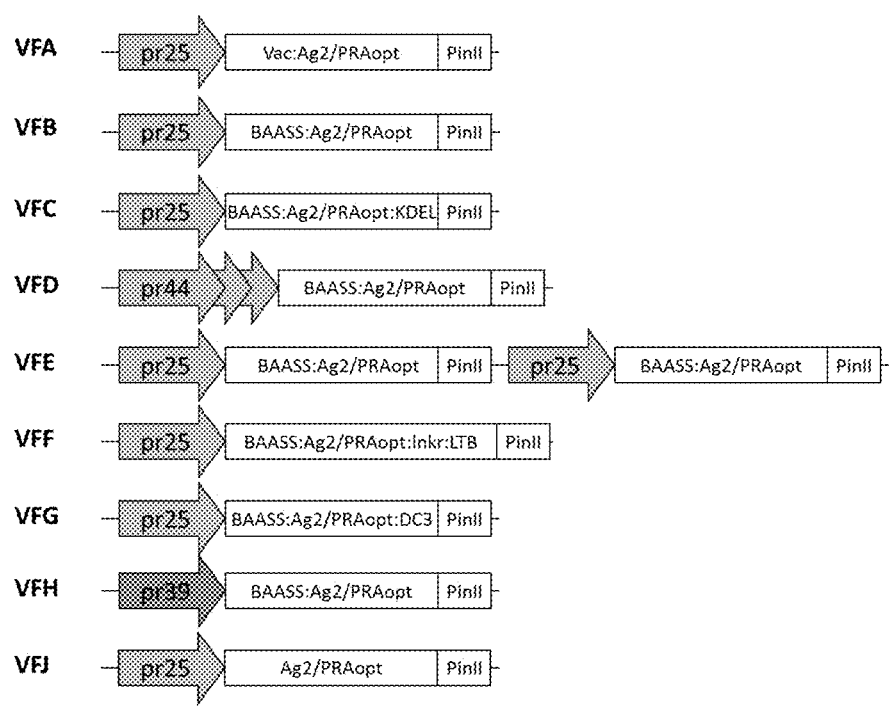
FIG. 2 is a graphic showing a schematic representation of rAg2 expression constructs. Nine plasmid constructs were designed to express recombinant Ag2 in maize. Tissue-preferential maize promoters (Pr25:seed embryo, Pr44:seed embryo, and Pr39:endosperm) were used to drive high Ag2 gene transcription and subsequent high yield of protein production. In various constructs, cellular/organelle-targeting sequences were added (Vac:vacuole, BAASS:cell wall) and C-terminus (KDEL:ER) to the codon-optimized Ag2 (Ag2opt). Immune-modulators, a heat labile enterotoxin B subunit (LTB) and a dendritic cell targeting sequence (DCpep) were fused to the C-terminus of Ag2opt as indicated for VFF and VFG constructs, respectively. Untranslated 3' region of a potato protease inhibitor II (pinII) was added to all constructs as a transcriptional termination element to enhance mRNA stability.
Figure 4A:
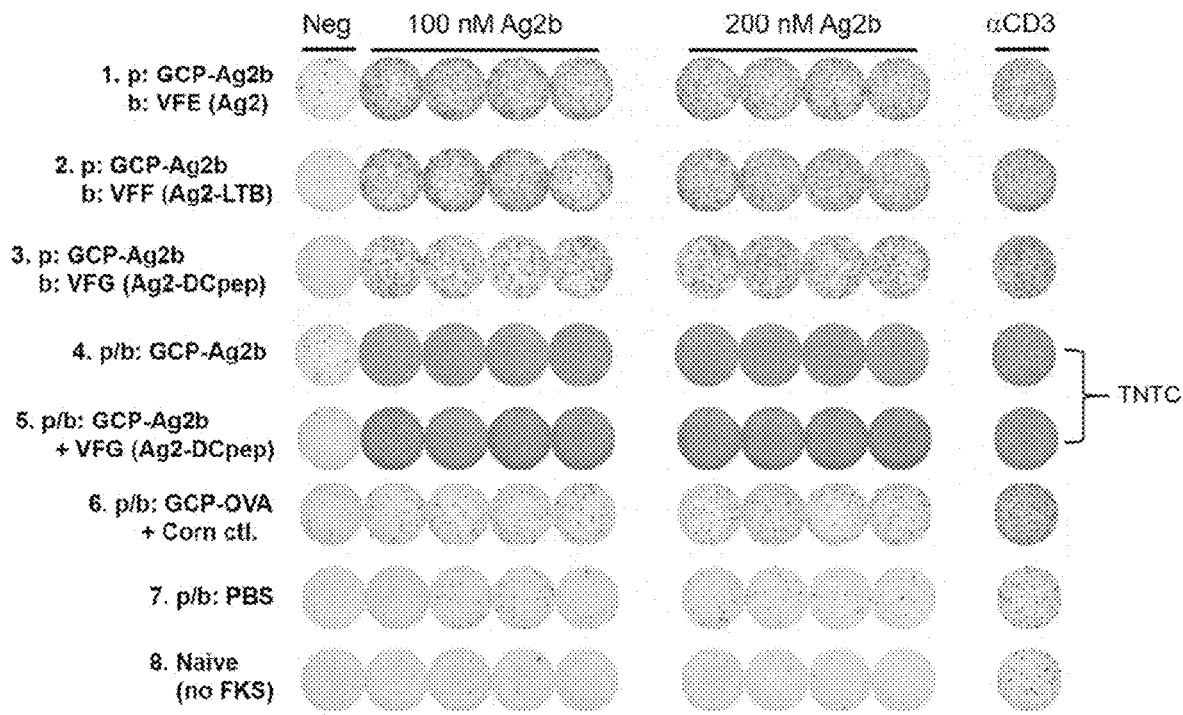
FIGS. 4A and B are an image of spot forming units (A) and a graph (B) showing results of vaccination with Ag2 induced cell-mediated Th17 immune response. Groups of mice received one priming (p) and 3 boosting (b) doses of vaccine formulations as indicated in panel A. Immunogenic vaccines include bacterium-expressed recombinant Ag2 encapsulated with glucan-chitin-particles (GCP-Ag2b) and 3 types of maize-derived Ag2 in the form of edible wafers (VFE, VFF and VFG). GCP-OVA, wafer contained no Ag2 (corn ctl.) and PBS alone were used for mock vaccination. Vaccines were administered by oral delivery for wafers and subcutaneous injection for GCP formulations. Vaccinated mice (groups 1-7) were challenged with formalin-killed-spherule (FKS) of Coccidioides posadasii and spleen removed for IL-17A ELISPOT analysis in a 96-well plate. Splenocytes were stimulated with Ag2b (100 and 200 nM), anti-CD3 antibody (αCD3) or untreated (Neg). Splenic cells that secreted IL-17A were visualized in (A) and quantified as spot forming units (B) with a maximal count of 3,000 per well. TNTC, too numerous to count.
Figure 4B:
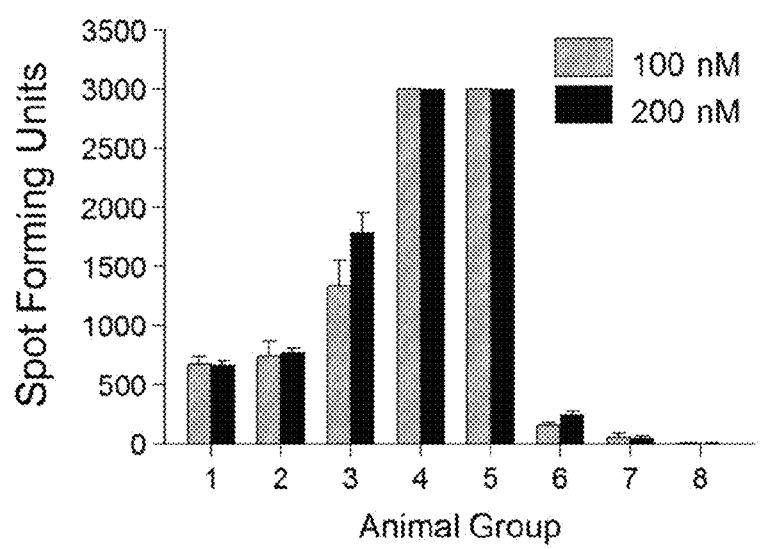
Figure 6:
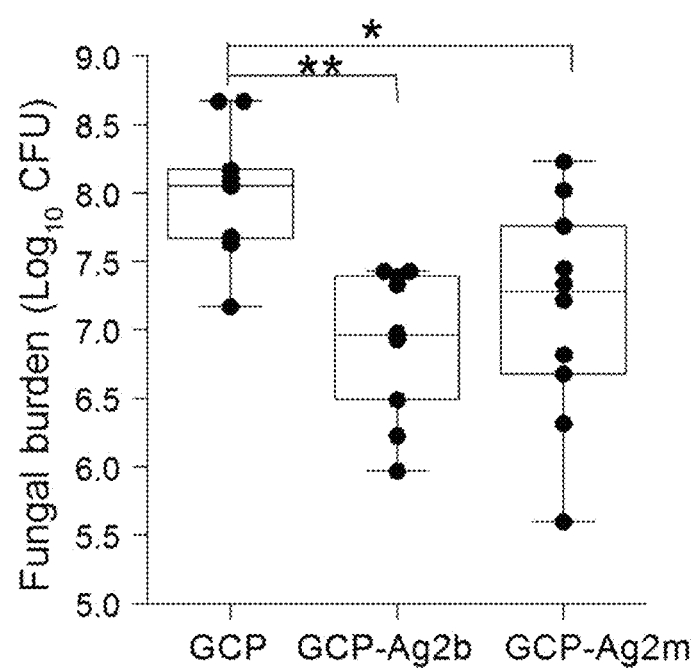
FIG. 6 is a graph showing results of immunization with bacterium- and maize-expressed Ag2 protection against pulmonary coccidioidomycosis. Mice (n=10 per group) were vaccinated with GCP-Ag2b, GCP-Ag2m or GCP alone and challenged intranasally with a lethal dose of C. posadasii. Lung fungal burden was measured at 14 days after challenge. $*p<0.05$, $**p<0.005$ by Mann-Whitney U test.
Figure 7:
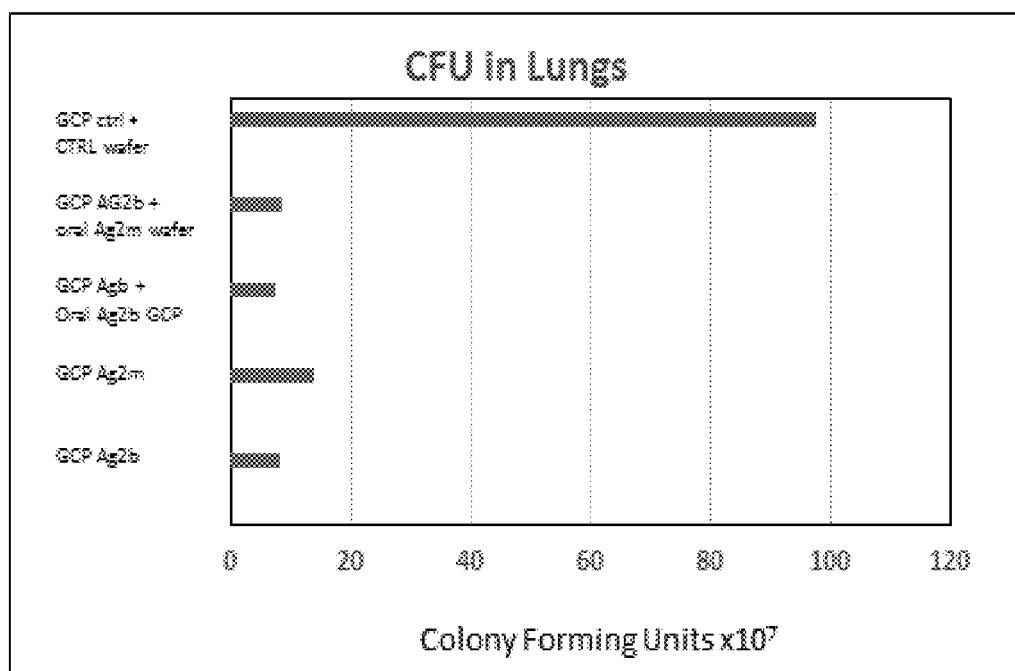
FIG. 7 is a graph showing fungal burden in lungs following challenge and administration of vaccines as indicated. Lung tissue was sampled to determine the amount of spores after the challenge. All treatments demonstrated a reduction in fungal burden compared to the negative control.
Figure 8:
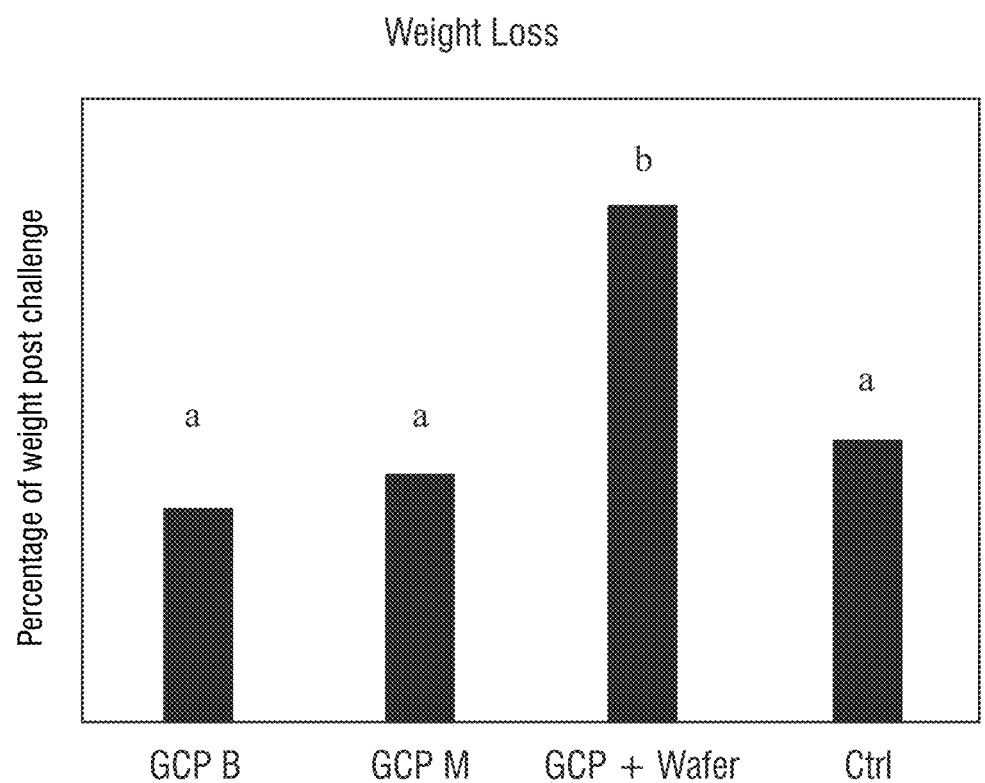
FIG. 8 is a chart showing weight post challenge.

The full-length Ag2 amino acid sequence (Genbank accession U39835) was codon-optimized for expression in maize, predicted splice sites and instability elements were screened for and removed, and a valine was placed directly preceding the Ag2 sequence in order to improve stability of the protein. (See SEQ ID NO: 1 and 2). All constructs contained promoters that preferentially accumulate protein in maize seed. Construct VFA (FIG. 2) was assembled with a 3 kb globulin 1 promoter sequence[20], which acts to produce protein in the embryo portion of the seed. The promoter was followed by a vacuolar targeting signal sequence, derived from a barley aleurain[21]. Construct VFB was constructed in the same manner as VFA but contained the barley alpha amylase signal sequence (BAASS) in order to target the protein to the cell wall. Construct VFC contained a third targeting signal, a combination of the BAASS at the N-terminus and a KDEL sequence at the C-terminus in order to target the protein to the endoplasmic reticulum (ER). A fourth construct, VFD, contained an enhanced globulin 1 promoter with three copies of the 5'-most 1745 bp promoter[22]. VFE was constructed with the same components as VFB with two copies of the transcription unit placed in tandem in a head-to-tail orientation. VFF was assembled in the same manner as the VFB construct, with a linker sequence connecting the Ag2 C-terminal sequence to the LTB N-terminal sequence (Genbank accession M17874). VFG also contained the same components as VFB, with the addition of a dendritic cell targeting sequence, DCpep[16], at the Ag2 C-terminus. VFH was modeled after VFB, but contained a promoter that expressed preferentially in the endosperm, the 27 kDa gamma-zein promoter[23]. Finally, transcription elements in VFJ were the same as in VFA, to the exclusion of a plant-derived targeting signal. Only the original fungal endogenous Ag2 targeting signal was included in this construct. All DNA construct coding sequences were followed by a potato protease inhibitor II (pinII) 3'-untranslated region for enhancing mRNA stability[24], and a glufosinate resistance gene which is a maize-optimized phosphinothricin N-acetyltransferase (pat) gene from *Streptomyces viridiochromogenes*[25] for selection of putative plant transformants. Ag2 transgenic constructs used for *E. coli* expression and purification were conducted as described previously[9]

Maize Transformation and Seed Propagation Constructs VFA to VFJ were transformed into *Agrobacterium tumefaciens* and maize, as described previously[26]. Selection of transformed lines was done by using bialaphos, and propagated as described previously[25, 27]. T1 seed was generated by crossing the ears of the transformed (T0) plants with the pollen of the transformation germplasm, HiII. T2 seed were generated by self-pollination of the T1 plants.

Purification of Ag2 from Bacteria and Production of Antibodies

*E. coli*-derived Ag2 was purified as previously described[9], with some modifications. In brief, *E. coli* containing the Ag2-expression plasmid were grown at 37° C. overnight in LB medium with antibiotic. This transformed bacterium overexpressed a thioredoxin-His(6x)-Ag2 fusion protein with a thrombin cleavage site between His(6x) and Ag2. The seed culture was used to inoculate two 1 L flasks containing 250 mL MagicMedia (ThermoFisher Scientific, Waltham, Mass.) with antibiotic and grown overnight. The cell pellets were harvested, ground with liquid nitrogen, resuspended in PBS, and treated with DNAseI. The pellet was then resuspended in 8M urea and centrifuged to collect the supernatant. The supernatant was then adjusted to 2M urea and the extract was loaded onto a Ni-NTA His-bind resin (Novagen). After washing with the same buffer, the column was treated with thrombin and the Ag2 was released from the column. The Ag2 in the eluate was confirmed by Coomassie gel electrophoresis. This material was then sent to Pacific Immunology to make rabbit polyclonal antibodies. The final bleed was used for all analysis.

Quantitation of Ag2 from Maize

Protein was extracted from either single T1 seeds or 100 mg±5 mg of ground T2 50-seed bulk material using 1 mL PBS+1% TritonX100 extraction buffer. Six single T1 seeds were sampled from each ear while 50-seed T2 bulks were assayed in duplicate. Percent total soluble protein in T1 seed were determined by measuring total soluble protein using a Bradford Assay. Estimated mg/kg were assessed by weighing the combined 6 seeds and calculating a mean weight for each seed. Antigen in the extract was detected using custom polyclonal anti-Ag2 antibodies that were generated in rabbit using purified Ag2 from E. coli[9]. A sandwich ELISA was developed in which the terminal bleed rabbit serum was used to coat ELISA plates. Plates were blocked with PBS+ 3% BSA, washed with PBS, and detection antibody was applied in PBS+3% BSA. Detection antibody was generated by purifying the serum antibody on a protein A column and biotinylating the resultant fraction of purified antibody (Innova Biosciences, Cambridge, UK). Streptavidin-AP and pNPP tablets were used to detect antibody binding to Ag2. The recombinant E coli-purified protein was used as a standard curve on all ELISAs.

Purification of Maize-Derived Ag2

Ag2 was extracted from ground maize material from VFG lines using PBS+1% TritonX-100. After extraction for 30 minutes on ice, the suspension was centrifuged and filtered to remove cell debris. The extracts were affinity purified using custom polyclonal antibodies bound to an AminoLink resin (Thermo Fisher Scientific, Waltham, Mass.) and elution of the Ag2 protein with glycine buffer pH 3 followed immediately with buffer neutralization. SDS-PAGE was performed using 10% gels (Bio-Rad #4561033) run with Tris/glycine/SDS running buffer (Bio-Rad, #1610732). For Western blotting, Two gels were run simultaneously, one stained using Coomasie Blue for molecular weight analysis and the other transferred to a Nitrocellulose membrane (Thermo Fisher Scientific) using the iBlot 2 system (Invitrogen) for immunoblotting detection. Custom rabbit polyclonal anti-Ag2 primary antibody was then applied to the nitrocellulose membrane, followed by AP-conjugated goat anti-rabbit IgG secondary antibody (Jackson ImmunoResearch #111-055-003, West Grove, Pa.), and BCIP/NBT liquid substrate (Sigma #B1911, St. Louis, Mo.) for Ag2 band visualization.

Preparation of Vaccine Candidates

Maize grain was ground into flour and formed into wafer-like tablets by adding water and confectioner's ultrafine sugar and drying the wafers in a vacuum oven as described previously[28] In brief, maize Ag2 wafers were produced from a mixture of 2.5 g±0.1 g ground T1 seed, 1.85 g±0.05 g of confectioner's sugar, and 0.6 g±0.05 g of water. They were formed in a custom hand press and dried at 55° C.±4° C. in a vacuum oven at 21.5" Hg±0.5" Hg in less than one hour. Control wafers were produced using ground non-transgenic maize material (G909) obtained from Grain Processing Corporation (Muscatine, Iowa) using the same method of wafer formation and drying as for active ingredient wafers. GCP particles used for injection were loaded with E. coli-purified Ag2, as described previously[17, 29]. Each dose consisted of 200 µg GCPs, 1 µg Ag2, and 25 µg mouse serum album. Ovalbumin (1 µg) was used as a positive control for loading of the particles. Maize-produced Ag2 GCP particles for immunization was made from purified material using seed from the VFG construct (Ag2: DCpep). The concentration of maize-produced Ag2 was much lower (~10% of that used from bacterial-produced Ag2) due to limitations in the amount of seed available at the time. Efficiency of protein loading was confirmed by SDS-PAGE.

Mouse Studies

Formalin-killed spherule (FKS) challenge study: Ten BALB/c mice, 5 males and 5 females, were assigned to each treatment. Immediately preceding the first day of each dose, all mice were fasted overnight. Treatment 1 consisted of a subcutaneous (sc) injection of 1 μg of *E. coli*-derived Ag2-loaded into 200 μg GCPs on day 0, and 15 g of oral VFE wafers for boosting doses delivered on days 14, 28, and 42. Mice were fed on wafers ad libitum, and wafers were administered for three consecutive days, 5 g per day per mouse, for each dose. Treatments 2 and 3 were the same as Treatment 1 except VFF and VFG wafers were fed to mice, respectively. Treatment 4 consisted of Ag2 GCP particle injection on days 0, 14, 28, and 42. Treatment 5 consisted of a combination of injected and VFG oral dose on all dosing days. Treatment 6 was control GCP particles and control wafers administered on all dosing days. Mice in Treatment 7 were injected with saline on all dosing days. Mice were then challenged with formalin-killed *Coccidioides* spherules on day 63 and sacrificed on day 70 to look at the T cell response in the lung and spleen. Blood was collected on days 0, 28, 54, and 70 to test for antibody production. Live arthroconidia challenge study: Treatment group size, mouse breed, and gender distribution was as in Mouse study 1. All doses were initiated on day 0 and 14 (one primary dose and one boosting dose), Mice were challenged with intranasal delivery of approximately 100 viable arthroconidia per mouse, carried out on day 42. Lung colony forming units (CFUs) were analyzed on day 56.

Anti Ag2 Antibody Detection

Induction of anti-Ag2 specific serum IgG and IgA following vaccination was assessed using a sandwich ELISA similar to that previously described[30]. In brief, ELISA plates were coated with *E. coli*-purified Ag2 in carbonate buffer at pH 9.6. Serum samples were diluted 1:100 for IgG and 1:30 for IgA. AP-conjugated anti-mouse IgG (Jackson Immunoresearch Laboratories, cat #115-055-008) or AP-conjugated anti-mouse IgA (Abcam, cat #134422) were used to detect IgG and IgA, respectively. A pNPP solution was then used to visualize results and read at an OD of 405 nm.

Splenocyte Recall Assay/IFN-Gamma and IL17A ELISPOT

Following terminal bleeds, spleens were dissected from 4 mice in each treatment and analyzed for cytokine production using a T-cell recall assay, as described previously[29]. Dissections were done in duplicate (spleens removed from an additional 4 mice in each group) to increase robustness of the analysis. IFN-γ and IL-17A cytokines were analyzed as indicators of Th1 and Th17 responses, respectively. Statistically significant differences between cytokine production in parenterally and orally vaccinated mice were determined using a Student t-test, as previously described[29].

Intracellular Cytokine Staining

Intracellular cytokine staining assays were conducted to determine the numbers of IFN-γ- and IL-17-producing $CD4^+$ T cells in lungs at 9 and 14 days post-challenge. Pulmonary leukocytes were isolated, as previously reported ([31]). Briefly, aliquots of pulmonary leukocytes were stimulated with anti-CD3 and CD28 in the presence of GolgiStop™ in 10% FBS complemented RPMI 1640 for 4 hours at 37° C. Permeabilized cells were stained with selected fluorochrome-conjugated monoclonal antibodies specific for CD4, CD8, IFNγ, or IL-17A to determine absolute numbers of the specific cytokine-producing $CD4^+$ T cells. The leukocytes were gated for CD4+ T cells and their levels of cytokine expression were determined. The absolute numbers of the specific cytokine-producing CD4+ T cells relative to the total lung-infiltrated leukocytes per lung homogenate was calculated by multiplying the percentage of each gated population by the total number of viable pulmonary leukocytes determined by hemocytometer counts, as previously reported. Student-Newman-Keuls test, a type of ANOVA statistical analysis for all pairwise comparisons was used to analyze percentages and numbers of specific cytokine-producing T cells in lungs of mice, as previously reported.

CFU Quantification

Lung fungal burden was assessed at day 56, 2 weeks post-challenge, as CFU/lung was evaluated as previously described[32] and the Mann-Whitney U test was applied for statistical analysis, as previously described[9].

Results

Accumulation of Ag2 in Maize

Previous work with other recombinant proteins has demonstrated several factors that influence accumulation in the host tissue including; optimized coding sequence, tissue-preferred promoters and subcellular targeting signals. In addition, carrier proteins have been shown to increase the immune response for some antigens. The additional sequence from the carrier protein also has the potential to influence the accumulation of the protein in the host. Therefore, the various seed-preferred constructs shown in FIG. 2 were created to test for Ag2 accumulation. Each construct was transformed into maize and seed harvested for evaluation. A total of 63 transformation events representing the various constructs were harvested.

The relative levels of Ag2 were estimated using an ELISA with the bacteria-produced Ag2 as the standard. Over 1500 seeds representing the various transformation events were analyzed individually and the mean of the top 10% of highest expressing seeds were used to rank the potential for each construct to overproduce the antigen[11]. The highest levels of Ag2 were from VFF (Ag2 fused to LT-B) with a mean of 1.95% of total soluble protein (TSP), or 475 mg/kg, and the highest recorded seed producing 3.99% TSP (1388 mg/kg) (FIG. 3). The next highest mean was from VFG (Ag2 fused to DCpep) with a mean Ag2 concentration of 1.09% TSP, or 256 mg/kg, and the highest single seed accumulating 3.07% TSP (711 mg/kg). Subcellular localization affected accumulation of Ag2, as demonstrated when comparing constructs VFA (plant vacuolar signal), VFB (plant cell wall signal) and VFC (plant ER signal). A construct with the native signal fungal Ag2 targeting signal was also compared to the plant signal sequence. The top 10% of expressing VFA and VFJ seed demonstrated the highest mean Ag2 accumulations of 0.11% and 0.10% TSP, respectively, VFB a mean Ag2 of 0.07% TSP and VFC seed the lowest mean of 0.04% TSP. Using an enhanced promoter in construct VFD, higher levels of Ag2 (0.20% TSP) could be obtained compared to VFB with the same subcellular location. Two transcription units in tandem (VFE) express somewhat more (0.10% TSP) than the equivalent single transcription unit (VFB). Driving Ag2 expression with an endosperm promoter (VFH) compared to an embryo promoter (VFB) resulted in approximately the same accumulation of recombinant antigen based on whole seed. VFF and VFG were clearly superior in over accumulation of Ag2 compared to all other constructs.

In the top lines, the level of accumulation in maize is over 500 mg/kg and in the best case over 1000 mg/kg. This represents levels of 100-fold higher than the best expression obtained in *E. coli* or yeast in the non-optimized maize lines. With these high levels of recombinant antigen in maize grain, economic feasibility of producing the purified antigen is a reality.

Western blot analysis was further used to determine protein integrity and the size of the recombinant Ag2 produced in maize. The results of representative seed extracts from selected constructs show all of the maize-derived Ag2 displayed a major band just slightly smaller in molecular weight to the *E. coli*-derived Ag2 with the exception of VFF that contains the LT-B fusion protein, which accounts for the much larger size.

Formulation of Ag2-Based Vaccines

Two types of Ag2 formulations were prepared for vaccine evaluation. One vaccine formulation is wafers made of Ag2-expressing corn seeds for oral delivery; the other is formulated for subcutaneous (s.c.) injection by encapsulation of soluble Ag2 with glucan-chitin-particles (GCP). To prepare maize wafers for oral delivery of the maize-derived Ag2, seed from VFE, VFF, and VFG representing Ag2, Ag2-LTB and Ag2-DCpep were bulked and ground to a flour-like consistency. These flours were then formed into wafer-like tablets.

Oral Doses.

Grain collected from VFE, VFF and VFG were ground separately into corn flour and passed through a 20-mesh sieve. 2.5 grams of flour was then combined with 1.25 grams of sucrose and formed into tablets using a tablet press. As there is a difference in the amount of Ag2 in the grain from the various constructs, the final concentrations of the bulk ground flour were determined by ELISA and used to calculate the amount of Ag2 per wafer. Assuming the mice consumed 5 grams of the maize grain this calculated to 0.15 mg Ag2, 2.5 mg Ag2:LTB and 2.25 mg for Ag2:DC3 (treatments 1, 2 and 3 below respectively). The antigens have been shown to be stable in this matrix and dosing animals in this range has proven an effective method to elicit a mucosal response for other vaccine candidates. (Hayden, et al. (2012) Bioencapsulation of the hepatitis B surface antigen and its use as an effective oral immunogen, Vaccine 30, 2937-2942.)

Injected Doses.

Purified rAg2 expressed in *E. coli* was encapsulated in Glucan Chitin Particles (GCPs) using the hydrodynamic loading method. (See, Mirza, et al. (2017) Beta-Glucan Particles as Vaccine Adjuvant Carriers, Vaccines for Invasive Fungal Infections: Methods and Protocols, 143-157.) Briefly, dry GCP (5 mg) was swollen with 25 μL of 10 mg/mL rAg2 and lyophilized. The species homologous carrier protein mouse serum albumin was then loaded into the GCPs. Following lyophilization the proteins were trapped using a yeast RNA trapping polymer to prepare the GCP encapsulated antigen vaccine. A dose of 10 micrograms was given subcutaneously to each animal. GCP vaccines are stable in serum, glucan receptor-targeted to antigen-presenting cells (APCs) and the antigen is readily released following phagocytosis by APCs leading to strong humoral and T-cell response, especially a mixed Th1/Th17 immunity. The combined targeted delivery-adjuvant properties have proven effective with a wide range of antigens. (Mizara (2017).)

Table 1 shows the Ag2 concentration in wafers for each construct and that no antigen was lost during the production of the wafers. Control wafers were included in the analysis and no Ag2 was detected in either the parent material or the wafers.

TABLE 1

Ag2 concentrations in Wafers used for oral vaccine delivery

| | parent material (mg/kg) | wafers (mg/kg in flour) |
|---|---|---|
| VFE | 7 | 10 |
| VFF | 165 | 173 |
| VFG | 158 | 153 |
| Control | Below detection | Below detection |

For vaccine candidates used for subcutaneous injection, the soluble Ag2-DCpep was isolated from the VFG seed extracts by anti-Ag2 affinity chromatography. FIG. 3B shows a Western blot of the seed extract and the eluate from the antibody column. Because of the limited amount of seed available at the time, there was not enough protein to be detected on a Coomassie stained gel. The purified maize Ag2-DCpep (~0.1 μg) was mixed with 25 μg mouse serum album and then encapsulated into GCPs (200 μg) to make the GCP-Ag2m vaccine (per dose). Similarly, we generated a GCP-Ag2b vaccine using bacterial expressed Ag2 (1 μg per dose) and a control GCP-OVA (1 μg ovalbumin per dose) without Ag2.

Vaccination of Mice with Maize-Derived Ag2 Induced Robust Cell-Mediated Immune Responses To assess Ag2 vaccination induced immune responses, we vaccinated 7 groups of mice with various vaccine formulations/regimens and challenged the mice with formalin-killed spherules (FKS) of *Coccidioides*. Spleen was collected to make splenocyte suspension for T-cell recall assay by IL-17A ELISPOT and lungs were used for immune T-cell recruitment/activation assessment by flow cytometry. All 7 groups of mice were received a prime vaccination followed by 3 booster doses 2 weeks apart. The first 4 groups of mice were primed with GCP-Ag2b by subcutaneous injection, and then boosted with orally delivered VFE (Ag2, group 1), VFF (Ag2-LTB, group 2), or VFG (Ag2-DCpep, group 3) wafers or s.c. injection of GCP-Ag2b (group 4). Mice in groups 5-7 received the same vaccinated materials for their priming and boosting doses, which consist of a combination of GCP-Ag2b (s.c.) and VFG wafers (oral) (group 5), a combination of GCP-OVA (s.c.) and control wafers without no Ag2 (oral) (group 6), and PBS (s.c. group 7). Mice fed on the wafers ad libitum and were estimated to ingest 0.1 mg of VFE Ag2, 1.5 mg of VFF, and 1.5 mg of VFG per dose, based on consumption estimates and wafer Ag2 concentrations.

Mice in all treatments were FKS-challenged 3 weeks after the last dose and assessed for immune response one week after the challenge. Naïve mice (group 8) without vaccination nor FKS challenge also were used as a control for immunoassays. Splenocytes from each group of mice were stimulated with Ag2b (100 and 200 nM; antigen-specific) and anti-CD3 (mitogenic positive control), or untreated (medium, negative control). Numbers of IL-17A secreting cells were quantified by ELISPOT assay. As shown in FIG. 4, minimal numbers of IL-17A secreting splenocytes were presented in all untreated samples; however, the numbers increased significantly in all groups upon anti-CD3 antibody treatment suggesting the obtained splenocytes were receptive to antigen stimulation. TH17 T-cells targeted to Ag2 were produced. It is evident that vaccination with 4 doses of GCP-Ag2b induced robust and highest Th17 cellular immune response (FIG. 4, groups 4 and 5). The conditions for the assay were at saturation for groups 4 and 5, therefore the extent of additive effect of oral VFG vaccination on inducing Th17 immunity remains unclear. Mice receiving booster doses by ingestion of the Ag2 fused to DCpep (Group 3, VFG material) showed an increased response over Ag2 alone or Ag2 fused to LTB (VFE and VFF, groups 1 and 2, respectively).

Similarly, priming and boosting with GCP-Ag2b (group 4) enhanced the recruitment of IFN-γ- (Th1) and IL-17A-producing T cells (FIG. 5). There was a slight increase in the response when combined with VFG oral vaccine (group 5) but this was not statistically significant. The assay was at or near maximal for both groups, therefore it was not possible to resolve the effect conclusively.

Serum was analyzed for IgG and a progressive increase in IgG was observed in mice for groups 1-5 with titers of $10^3$ for groups 1-3 and $10^4$ for groups 4 and 5 (data not shown). A significant increase in serum IgA was only detected in group 4 and 5 mice.

Vaccination with Purified Maize-Expressed Recombinant Ag2m Reduced Fungal Burden Following Pulmonary *C. posadasii* Challenge Ingestion of rAg2-DCpep expressing VFG wafer seems to slightly enhanced Th1 and Th17 response (FIG. 4, group 3 and FIG. 5 group 5), that are critical for control of pulmonary *Coccidioides* infection. To further assess the protective efficacy of rAg2-DCpep, we purified the antigen from VFG corn seeds by anti-Ag2 affinity chromatography and formulated a GCP-Ag2m vaccine. Groups of mice (n=10) were vaccinated twice with GCP-Ag2m, GCP-Ag2b or GCP without Ag2 by s.c. injection and challenged intranasally with a lethal dose of *C. posadasii* 2 weeks after the booster. Fungal burden in the lungs were assessed at day 14 post challenge. As shown in FIG. 6, Compared to GCP-alone vaccination, GCP-Ag2b and GCP-Ag2m were able to significantly reduce the fungal burden in the lungs by an average of 92% and 82%, respectively. It is noted that GCP-Ag2m contains only approximately 0.1 μg of Ag2-DCpep, while GCP-Ag2b consist of 1 μg Ag2 per vaccine dose. There was no significant difference in the reduction of fungal burden between maize and bacteria-produced Ag2.

The body weight of mice were monitored prior to and after fungal challenge. When mice were administered the paired dosing (oral and s.c.), this was the only treatment that reduced the loss of body weight (FIG. 8). This confirms earlier results from above that the paired dosing can improve the efficacy of the vaccination.

Discussion

The GPI-anchored antigen, Ag2, is a likely candidate for a subunit vaccine for Valley Fever, but its poor accumulation in microbial hosts hinders commercialization. Therefore, maize, which has been used for other problematic recombinant proteins was attempted as an alternative host. For many recombinant proteins including the hepatitis B surface antigen (HBsAg), the protein is most highly accumulated when using an embryo preferred cell wall targeting signal[22, 30]. In some cases, such as the LTB antigen, it is most highly accumulated when using a vacuolar targeting signal. Fusion to LTB can also increase accumulation of recombinant proteins[20] (and unpublished results). The ER has shown to be the preferred location for yet other recombinant proteins such as cellulases[33]. While the most success has come when targeted to the embryo, butyrylcholinesterase is a case where the highest accumulation occurred when using an endosperm-preferred promoter and an ER-targeting signal[34].

This led to the evaluation of constructs targeting these different tissues and intracellular locations. For the Ag2 recombinant protein, we established that the vacuolar targeting sequence produces the highest levels of accumulation. We also observed that a fusion protein at the C-terminal end of Ag2 can increase accumulation by more than 10-fold, presumably due to stabilization of the protein. This effect does not require a large string of amino acid sequences as the DCpep is only 12 amino acids long, but accumulation was greatly enhanced by the longer sequence in the LTB-fused Ag2 construct. Some of this stabilization may be related to whether the C-terminal GPI anchoring signal is cleaved from the Ag2 protein.

Analysis on Western gels of the maize-produced Ag2 showed that most constructs had a cross reacting band slightly smaller than that of Ag2 produced in bacteria. As can be seen in the Western blot (FIG. 3B), construct VFE displays a doublet, with the presumed uncleaved protein retaining the GPI anchor as the top band, and the GPI anchor-cleaved protein as the smaller band. This hypothesis is supported by the fact that the VFG lines (Ag2:DCpep) show a more intense top band, and GPI anchor prediction programs fail to predict cleavage once the peptide is added to the C terminus of Ag2. Interestingly, although accumulation levels of Ag2 in the embryo and endosperm seem to be approximately equivalent by ELISA, the endosperm-targeted Ag2 seems to undergo degradation or proteolysis, as shown in FIG. 3. A much more detailed physical analysis of the recombinant protein is planned to clarify the differences in protein structure.

Some VFF first generation single seed demonstrated levels greater than 1,000 mg/kg for the recombinant antigen. Optimization of recombinant proteins in maize have shown a minimum of a 10-fold increase and there are examples of proteins yielding 2 g/kg in whole seed[11]. The recombinant protein concentration can be further increased another 7-fold by fractionation of the seed by retaining the embryo fraction. These levels of improvement by breeding and fractionation have been obtained for other recombinant proteins, such as HBsAg[22] and LTB[35]. These accumulation levels hold great promise for a low cost subunit vaccine as they should be greater than 100-fold higher than when produced in E. coli.

Grain from one of the constructs, VFG, was used to purify the antigen using an antibody affinity column. This approach appeared to be a useful method for analytical purposes. However, for large-scale production, a more conventional purification will be established using ionic exchange columns and size chromatography. The much higher concentrations, seen in maize grain should make this possible and will be pursued in the future.

All indications to date show that maize could be a useful host to accumulate the Ag2 but a much more in depth physical characterization is undertaken. Prior to undertaking this detailed study, we will investigate further a key assumption; specifically, is the immune response elicited with maize-produced material comparable to that of Ag2 made in microbes. When the purified maize-produced Ag2 was compared with the bacterial produced Ag2, both showed a reduction in the fungal burden after challenge when administered in GCPs subcutaneously. A more detailed study is undertaken to understand whether there are quantitative differences, however the maize-derived material appears to be an effective immunogen.

Having an ample supply of antigen is a key requirement for subunit vaccines but it is also critical to understand the best way to administer the vaccine to provide a protective response. Previous work has shown that for this pathogen, a strong mucosal response is required. Most traditional vaccines are parenterally administered which provides little or no mucosal immune response. Previous reports have demonstrated that GCP particles can induce strong Th1 and Th17 responses, indicative of protection[19] using a Coccidioides antigen. This was confirmed in this study and both maize and E. coli derived Ag2 were able to reduce the fungal load in the lungs.

Reports using orally-delivered maize grain have also shown success in eliciting a strong mucosal response for other antigens. Therefore, a combination of oral and GCP injected vaccine candidates were tested to determine whether a strong protective immune response could be obtained[36, 37]. The FKS challenge showed that the oral wafers using the DCpep provided a better Th17 response in splenocytes than the other wafers tested. This is not likely due to concentration alone as the VFF material had the same concentration of Ag2 therefore the DCpep may enhance the immune response.

The combination of GCPs and oral wafers may have had an improvement over injected doses alone however, due to the fact that immune response detection methods used were saturated in the FKS challenge study, it was not possible to determine whether this was significant. However, the reduction of the loss of body weight when challenged confirms that this is a more efficacious approach. With the future abundance of Ag2-grain, more detailed studies will be undertaken to evaluate the effect of higher concentrations of orally administered wafers and maize-derived Ag2 loaded into GCPs.

Conclusion

High levels of Ag2 in maize grain have been developed which promise to produce Ag2 at concentrations of grams of Ag2/kg grain. These lines have the potential for economically feasible production of the protein for a commercial vaccine. The mouse model indicates that the maize-produced Ag2 protein can provide protection from the pathogen. Additional studies are undertaken; a) optimize Ag2 accumulation in maize, b) develop an efficient purification process, c) characterize the Ag2 from maize and d) develop the optimal vaccination regime.

REFERENCES FOR EXAMPLES 2-3

[1] Tarcha, E. J., Basrur, V., Hung, C.-Y., Gardner, M. J., and Cole, G. T. (2006) Multivalent recombinant protein vaccine against coccidioidomycosis, *Infect Immun* 74, 5802-5813.
[2] Smith, C. E., and Beard, R. R. (1946) Varieties of coccidioidal infection in relation to the epidemiology and control of the diseases, *American Journal of Public Health and the Nations Health* 36, 1394-1402.
[3] Nguyen, C., Barker, B. M., Hoover, S., Nix, D. E., Ampel, N. M., Frelinger, J. A., Orbach, M. J., and Galgiani, J. N. (2013) Recent advances in our understanding of the environmental, epidemiological, immunological, and clinical dimensions of coccidioidomycosis, *Clinical Microbiology Reviews* 26, 505-525.
[4] Pappagianis, D. (2001) Seeking a Vaccine against *Coccidioides immitis* and Serologic Studies: Expectations and Realities, *Fungal Genetics and Biology* 32, 1-9.
[5] Borchers, A. T., and Gershwin, M. E. (2010) The immune response in Coccidioidomycosis, *Autoimmunity Reviews* 10, 94-102.
[6] Fisher, B. T., Chiller, T. M., Prasad, P. A., Beveridge, M., Walsh, T. J., and Zaoutis, T. E. (2010) Hospitalizations for coccidioidomycosis at forty-one children's hospitals in the United States, *The Pediatric Infectious Disease Journal* 29, 243-247.

[7] CDC. (2013) Increase in reported coccidioidomycosis—United States, 1998-2011, *Morbidity and Mortality Weekly Report* 62, 217-221.

[8] Cole, G. T., Hung, C.-Y., Sanderson, S. D., Hurtgen, B. J., Wüthrich, M., Klein, B. S., Deepe, G. S., Ostroff, G. R., and Levitz, S. M. (2013) Novel strategies to enhance vaccine immunity against coccidioidomycosis, *PLoS pathogens* 9, e1003768.

[9] Herr, R. A., Hung, C.-Y., and Cole, G. T. (2007) Evaluation of two homologous proline-rich proteins of *Coccidioides posadasii* as candidate vaccines against coccidioidomycosis, *Infect Immun* 75, 5777-5787.

[10] Shubitz, L. F., Yu, J.-J., Hung, C.-Y., Kirkland, T. N., Peng, T., Perrill, R., Simons, J., Xue, J., Herr, R. A., and Cole, G. T. (2006) Improved protection of mice against lethal respiratory infection with *Coccidioides posadasii* using two recombinant antigens expressed as a single protein, *Vaccine* 24, 5904-5911.

[11] Hood, E. E., Devaiah, S. P., Fake, G., Egelkrout, E., Teoh, K. T., Requesens, D. V., Hayden, C., Hood, K. R., Pappu, K. M., and Carroll, J. (2012) Manipulating corn germplasm to increase recombinant protein accumulation, *Plant biotechnology journal* 10, 20-30.

[12] Masarik, M., Kizek, R., Kramer, K. J., Billova, S., Brazdova, M., Vacek, J., Bailey, M., Jelen, F., and Howard, J. A. (2003) Application of avidin-biotin technology and adsorptive transfer stripping square-wave voltammetry for detection of DNA hybridization and avidin in transgenic avidin maize, *Anal Chem* 75, 2663-2669.

[13] Howard, J. A., and Hood, E. E. (2016) *Commercial Plant-produced Recombinant Protein Products*, Springer.

[14] Paul, M., and Ma, J. K. (2010) Plant-made immunogens and effective delivery strategies, *Expert Reviews* 9, 821-833.

[15] Tacket, C. O., Pasetti, M. F., Edelman, R., Howard, J. A., and Streatfield, S. (2004) Immunogenicity of recombinant LT-B delivered orally to humans in transgenic corn, *Vaccine* 22, 4385-4389.

[16] Mohamadzadeh, M., Duong, T., Sandwick, S. J., Hoover, T., and Klaenhammer, T. R. (2009) Dendritic cell targeting of *Bacillus anthracis* protective antigen expressed by *Lactobacillus acidophilus* protects mice from lethal challenge, *Proc Natl Acad Sci USA* 106, 4331-4336.

[17] Mirza, Z., Soto, E. R., Dikengil, F., Levitz, S. M., and Ostroff, G. R. (2017) Beta-Glucan Particles as Vaccine Adjuvant Carriers, *Vaccines for Invasive Fungal Infections: Methods and Protocols,* 143-157.

[18] Huang, H., Ostroff, G. R., Lee, C. K., Specht, C. A., and Levitz, S. M. (2013) Characterization and optimization of the glucan particle-based vaccine platform, *Clinical and Vaccine Immunology* 20, 1585-1591.

[19] Hung, C.-Y., Zhang, H., Castro-Lopez, N., Ostroff, G. R., Khoshlenar, P., Abraham, A., Cole, G. T., Negron, A., Forsthuber, T., and Peng, T. (2018) Glucan-chitin particles enhance Th17 response and improve protective efficacy of a multivalent antigen (rCpa1) against pulmonary *Coccidioides posadasii* infection, *Infect Immun*, IAI. 00070-00018.

[20] Streatfield, S., Jilka, J., Hood, E., Turner, D., Bailey, M., Mayor, J., Woodard, S., Beifuss, K., Horn, M., and Delaney, D. (2001) Plant-based vaccines: unique advantages, *Vaccine* 19, 2742-2748.

[21] Holwerda, B. C., Padgett, H. S., and Rogers, J. C. (1992) Proaleurain vacuolar targeting is mediated by short contiguous peptide interactions, *The Plant Cell* 4, 307-318.

[22] Hayden, C. A., Egelkrout, E. M., Moscoso, A. M., Enrique, C., Keener, T. K., Jimenez-Flores, R., Wong, J. C., and Howard, J. A. (2012) Production of highly concentrated, heat-stable hepatitis B surface antigen in maize, *Plant biotechnology journal* 10, 979-984.

[23] Russell, D. A., and Fromm, M. E. (1997) Tissue-specific expression in transgenic maize of four endosperm promoters from maize and rice, *Transgenic research* 6, 157-168.

[24] An, G., Mitra, A., Choi, H. K., Costa, M. A., An, K., Thornburg, R. W., and Ryan, C. A. (1989) Functional analysis of the 3'control region of the potato wound-inducible proteinase inhibitor II gene, *The Plant Cell* 1, 115-122.

[25] Streatfield, S. J., Mayor, J. M., Barker, D. K., Brooks, C., Lamphear, B. J., Woodard, S. L., Beifuss, K. K., Vicuna, D. V., Massey, L. A., and Horn, M. E. (2002) Development of an edible subunit vaccine in corn against enterotoxigenic strains of *Escherichia coli, In Vitro Cellular & Developmental Biology-Plant* 38, 11-17.

[26] Hood, E. E., Bailey, M. R., Beifuss, K., Magallanes-Lundback, M., Horn, M. E., Callaway, E., Drees, C., Delaney, D. E., Clough, R., and Howard, J. A. (2003) Criteria for high-level expression of a fungal laccase gene in transgenic maize, *Plant Biotechnology Journal* 1, 129-140.

[27] Streatfield, S. J., Jilka, J. M., Hood, E. E., Turner, D. D., Bailey, M. R., Mayor, J. M., Woodard, S. L., Beifuss, K. K., Horn, M. E., Delaney, D. E., and Howard, J. A. (2001) Plant-based vaccines: unique advantages, *Vaccine* 19, 2742-2748.

[28] Hayden, C., Smith, E., Turner, D. D., Keener, T. K., Wong, J. C., Walker, J. H., Tizard, I. R., Jimenez-Flores, R., and Howard, J. A. (2014) Supercritical Fluid Extraction Provides an Enhancement to the Immune Response for Orally-Delivered Hepatitis B Surface Antigen, *Vaccine in press.*

[29] Hurtgen, B. J., Hung, C.-Y., Ostroff, G. R., Levitz, S. M., and Cole, G. T. (2012) Construction and evaluation of a novel recombinant T cell epitope-based vaccine against coccidioidomycosis, *Infect Immun* 80, 3960-3974.

[30] Hayden, C. A., Streatfield, S. J., Lamphear, B. J., Fake, G. M., Keener, T. K., Walker, J. H., Clements, J. D., Turner, D. D., Tizard, I. R., and Howard, J. A. (2012) Bioencapsulation of the hepatitis B surface antigen and its use as an effective oral immunogen, *Vaccine* 30, 2937-2942.

[31] Hung, C.-Y., Gonzalez, A., Wüthrich, M., Klein, B. S., and Cole, G. T. (2011) Vaccine immunity to coccidioidomycosis occurs by early activation of three signal pathways of T helper cell response (Th1, Th2, and Th17), *Infection and Immunity* 79, 4511-4522.

[32] Delgado, N., Xue, J., Yu, J.-J., Hung, C.-Y., and Cole, G. T. (2003) A recombinant β-1, 3-glucanosyltransferase homolog of *Coccidioides posadasii* protects mice against coccidioidomycosis, *Infection and Immunity* 71, 3010-3019.

[33] Hood, E., Love, R., Lane, J., Bray, J., Clough, R., Pappu, K., Drees, C., Hood, K., Yoon, S., and Ahmad, A. (2007) Subcellular targeting is a key condition for high-level accumulation of cellulase protein in transgenic maize seed, *Plant biotechnology journal* 5, 709-719.

[34] Egelkrout, E., Hayden, C., Wales, M., Walker, J., Novikov, B., Grimsley, J., and Howard, J. (2017) Production of the bioscavenger butyrylcholinesterase in maize, *Molecular Breeding* 37, 136.

[35] Lamphear, B., Streatfield, S., Jilka, J., Brooks, C., Barker, D., Turner, D., Delaney, D., Garcia, M., Wiggins, B., and Woodard, S. (2002) Delivery of subunit vaccines in maize seed, *Journal of Controlled Release* 85, 169-180.

[36] Wu, H., Singh, N. K., Locy, R. D., Scissum-Gunn, K., and Giambrone, J. J. (2004) Immunization of chickens with VP2 protein of infectious bursal disease virus expressed in *Arabidopsis thaliana*, *Avian Diseases* 48, 663-668.

[37] Lappalainen, S., Pastor, A. R., Malm, M., Lopez-Guerrero, V., Esquivel-Guadarrama, F., Palomares, L. A., Vesikari, T., and Blazevic, V. (2015) Protection against live rotavirus challenge in mice induced by parenteral and mucosal delivery of VP6 subunit rotavirus vaccine, *Archives of Virology*, 1-4.

Sequences
SEQ ID NO: 1 Ag2 nucleotide sequence
SEQ ID NO: 2 Ag2 polypeptide sequence
SEQ ID NO: 3 DC3 polypeptide
SEQ ID NO: 4 DC3 nucleotide sequence
SEQ ID NO: 5 Linker used in experiments
SEQ ID NO: 6 LtB nucleotide sequence
SEQ ID NO: 7 LtB polypeptide sequence
SEQ ID NO: 8 Ag2 nucleotide sequence of GenBank U32518.1
SEQ ID NO: 9 Ag2 nucleotide sequence of GenBank U39835.1
SEQ ID NO: 10 Ag2 polypeptide sequence of XP_003069153.1
SEQ ID NO: 11 Ag2 polypeptide sequence of XP_001240075.1
SEQ ID NO: 12 Pr25 promoter
SEQ ID NO: 13 PR39 maize 27 kD gamma-zein gene promoter
SEQ ID NO: 14 pr44 promoter
SEQ ID NO: 15 Barley alpha amylase signal sequence
SEQ ID NO: 16 vacuole signal sequence
SEQ ID NO: 17 endoplasmic reticulum signal sequence
SEQ ID NO: 18 coding sequence of SEQ ID NO: 8

What is claimed is:

1. A vaccine for producing a protective response to *Coccidioides* sp., comprising,
   a plant or plant part, said plant or plant part comprising,
   i) a promoter preferentially directing expression to seed tissue of said plant or plant part; and
   ii) a nucleic acid molecule encoding an antigen 2 (Ag2) polypeptide of said *Coccidioides* sp. operably linked to said promoter and expressing said Ag2 polypeptide, wherein said Ag2 polypeptide is fused to a dendritic cell targeting (DC) peptide or a heat labile enterotoxin B subunit (LtB) peptide, and wherein said Ag2 polypeptide is expressed in said plant or plant part at levels of at least 50 mg/kg;
   wherein said vaccine comprising said plant or plant part comprises said Ag2 polypeptide and when administered to an animal produces a protective response in said animal.

2. The vaccine of claim 1, wherein said nucleic acid molecule further encodes a sequence targeting the Ag2 polypeptide to the cell wall, to the vacuole or to the endoplasmic reticulum.

3. The vaccine of claim 1, wherein said Ag2 polypeptide is fused to a DC3 peptide.

4. The vaccine of claim 1, wherein said Ag2 polypeptide is fused to a LtB peptide.

5. The vaccine of claim 3, wherein said DC peptide comprises SEQ ID NO: 3 or is encoded by SEQ ID NO: 4.

6. The method of claim 4 wherein LtB peptide comprises SEQ ID NO: 7 or is encoded by SEQ ID NO: 6.

7. The vaccine of claim 1, wherein said AG2 polypeptide comprises SEQ ID NO: 2, 10, 11 or 18, or is encoded by SEQ ID NO: 1, 8 or 9.

8. The vaccine of claim 1, wherein said vaccine when administered to an animal produces TH17 T-cells targeted to Ag2.

9. A method of expressing a polypeptide of *Coccidioides* sp., the method comprising,
   a) introducing into a plant or plant part
      (i) a promoter preferentially directing expression to seed tissue of a plant;
      (ii) a nucleic acid molecule encoding an Ag2 polypeptide of said *Coccidioides* sp. operably linked to said promoter, wherein said Ag2 polypeptide is fused to a dendritic cell targeting (DC) peptide or a heat labile enterotoxin B subunit (LtB) peptide; and
   b) expressing said Ag2 polypeptide in said plant, wherein said Ag2 polypeptide is expressed in said plant or plant part at levels of at least 50 mg/kg.

10. The method of claim 9, wherein said nucleic acid molecule further encodes a sequence targeting the Ag2 polypeptide to the cell wall, to the vacuole or to the endoplasmic reticulum.

11. The method of claim 9, wherein said DC peptide comprises SEQ ID NO: 3 or is encoded by SEQ ID NO: 4 and wherein LtB peptide comprises SEQ ID NO: 7 or is encoded by SEQ ID NO: 6.

12. The method of claim 9, wherein said Ag2 polypeptide comprises SEQ ID NO: 2, 10, 11 or 18, or is encoded by SEQ ID NO: 1, 8 or 9.

13. A method of producing a protective response in an animal comprising administering the vaccine of claim 1 to said animal and producing a protective response.

14. The vaccine of claim 1, wherein said Ag2 polypeptide is expressed in said plant or plant part at levels of at least 100 mg/kg.

* * * * *

SEQUENCE LISTING

```
<160> NUMBER OF SEQ ID NOS: 18

<210> SEQ ID NO 1
<211> LENGTH: 582
<212> TYPE: DNA
<213> ORGANISM: Coccidioides sp.

<400> SEQUENCE: 1
gtgcagttca gccacgctct catcgctctc gtcgctgccg gcctcgccag

```
Asp Gln Cys Ser Lys Ala Gly Val Pro Ile Asp Ile Pro Pro Val Asp
                85                  90                  95

Thr Thr Ala Ala Pro Glu Pro Ser Glu Thr Ala Glu Pro Thr Ala Glu
            100                 105                 110

Pro Thr Glu Glu Pro Thr Ala Glu Pro Thr Ala Glu Pro Thr Ala Glu
        115                 120                 125

Pro Thr His Glu Pro Thr Glu Glu Pro Thr Ala Val Pro Thr Gly Thr
    130                 135                 140

Gly Gly Gly Val Pro Thr Gly Thr Gly Ser Phe Thr Val Thr Gly Arg
145                 150                 155                 160

Pro Thr Ala Ser Thr Pro Ala Glu Phe Pro Gly Ala Gly Ser Asn Val
                165                 170                 175

Arg Ala Ser Val Gly Gly Ile Ala Ala Ala Leu Leu Gly Leu Ala Ala
                180                 185                 190

Tyr Leu

<210> SEQ ID NO 3
<211> LENGTH: 12
<212> TYPE: PRT
<213> ORGANISM: Artificial Sequence
<220> FEATURE:
<223> OTHER INFORMATION: DC3 polypeptide sequence

<400> SEQUENCE: 3

Phe Tyr Pro Ser Tyr His Ser Thr Pro Gln Arg Pro
1               5                   10

<210> SEQ ID NO 4
<211> LENGTH: 36
<212> TYPE: DNA
<213> ORGANISM: Artificial Sequence
<220> FEATURE:
<223> OTHER INFORMATION: DC3 nucleotide sequence

<400> SEQUENCE: 4
ttctacccct cctaccacag cacccccacag cgcccc                          36

<210> SEQ ID NO 5
<211> LENGTH: 24
<212> TYPE: DNA
<213> ORGANISM: Artificial Sequence
<220> FEATURE:
<223> OTHER INFORMATION: Linker sequence

<400> SEQUENCE: 5
gtcgacccga gggtgccgag ctcc                                        24

<210> SEQ ID NO 6
<211> LENGTH: 312
<212> TYPE: DNA
<213> ORGANISM: Escherichia coli

<400> SEQUENCE: 6
ggcgccccgc agtccatcac cgagctctgc tccgagtacc acaacaccca gatctacacc     60
atcaacgaca agatcctctc ctacaccgag agcatggccg gcaagcgcga gatggtgatc    120
atcaccttca gtccggcgc caccttccag gtggaggtgc cgggctccca gcacatcgac    180
tcccagaaga aggccatcga gcgcatgaag gacaccctcc gcatcaccta cctcaccgag    240
accaagatcg acaagctctg cgtgtggaac aacaagaccc cgaactccat cgccgccatc    300
agcatggaga ac                                                       312
```

<210> SEQ ID NO 7
<211> LENGTH: 104
<212> TYPE: PRT
<213> ORGANISM: Escherichia coli

<400> SEQUENCE: 7

```
Gly Ala Pro Gln Ser Ile Thr Glu Leu Cys Ser Glu Tyr His Asn Thr
1               5                   10                  15
Gln Ile Tyr Thr Ile Asn Asp Lys Ile Leu Ser Tyr Thr Glu Ser Met
            20                  25                  30
Ala Gly Lys Arg Glu Met Val Ile Ile Thr Phe Lys Ser Gly Ala Thr
        35                  40                  45
Phe Gln Val Glu Val Pro Gly Ser Gln His Ile Asp Ser Gln Lys Lys
    50                  55                  60
Ala Ile Glu Arg Met Lys Asp Thr Leu Arg Ile Thr Tyr Leu Thr Glu
65                  70                  75                  80
Thr Lys Ile Asp Lys Leu Cys Val Trp Asn Asn Lys Thr Pro Asn Ser
                85                  90                  95
Ile Ala Ala Ile Ser Met Glu Asn
            100
```

<210> SEQ ID NO 8
<211> LENGTH: 1234
<212> TYPE: DNA
<213> ORGANISM: Coccidioides sp.

<400> SEQUENCE: 8

```
ctctccctcc cccttagtcc ttcagttatt ttccttcccc atataaaaac atacattcgt      60
ttcgtggtcc atcaaagact atcgttaatt ctccaacccc ggttgtcgtt ttttttgctg     120
tactattagg gaggataatc gttctcgtcc gttagacgca catacataat caaaatgcag     180
ttctctcacg ctctcatcgc tctcgtcgct gccggcctcg ccagtgccca gctcccagac     240
atcccacctt gcgctctcaa ctgcttcgtt gaggctctcg gcaacgatgg ctgcactcgc     300
ttgaccgact tcaagtgcca ctgctccaag cctgagctcc caggacagat cactccttgc     360
gttgaggagg cctgccctct cgacgcccgt atctccgtct ccaacatcgt cgttgaccag     420
tgctccaagg ccggtgtccc aattgacatc ccaccagttg acaccaccgc cgctcccgag     480
ccatccgaga ccgctgagcc caccgctgag ccaaccgagg agcccactgc cgagcctacc     540
gctgagccca ccgctgagcc gactcatgag cccaccgagg agcccactgc cgtcccaacc     600
ggcactggcg gtggtgtccc cactggcacc ggttccttca ccgtcactgg cagaccaact     660
gcctccaccc cagctgagtt cccaggtgct ggctccaacg tccgtgccag cgttggcggc     720
attgctgctg ctctcctcgg tctcgctgcc tacctgtaaa tttagactat cagcaaaact     780
gacaagcacg tcgccatggc gtcaattatt ccccccgcgc atttttccca gttcattttt     840
ttctcgacaa caattcagca cgcattggaa ggcgaaatga cccggatgtc cgcaacacga     900
taaaaggttt cacgatctct cttctctgct ctcccctctc tgggaggctc taagtttcat     960
ttggattgaa atggggcgat gggcaatcgt tcgttggggg tgaagggagt ggggatctgg    1020
gattcgggat tcccgaaagt caaaaacgct ttattctgcg atgtgaccac ggctatgggt    1080
gtacaatgtt gtgtctgtga cttttttacg gggggggaga aacgaatata acacacctga    1140
tttcacttca cacttattac ttatcctgta tctaattgac atctgggaaa gggagcttat    1200
ttccctgtta ataatttggt gttatatttt gtta                                1234
```

<210> SEQ ID NO 9
<211> LENGTH: 1201
<212> TYPE: DNA
<213> ORGANISM: Coccidioides sp.

<400> SEQUENCE: 9

```

```
Pro Thr Glu Glu Pro Thr Ala Glu Pro Thr Ala Glu
        115                 120                 125

Pro Thr His Glu Pro Thr Glu Glu Pro Thr Ala Val Pro Thr Gly Thr
        130                 135                 140

Gly Gly Gly Val Pro Thr Gly Thr Gly Ser Phe Thr Val Thr Gly Arg
145                 150                 155                 160

Pro Thr Ala Ser Thr Pro Ala Glu Phe Pro Gly Ala Gly Ser Asn Val
                165                 170                 175

Arg Ala Ser Val Gly Gly Ile Ala Ala Ala Leu Leu Gly Leu Ala Ala
                180                 185                 190

Tyr Leu

<210> SEQ ID NO 11
<211> LENGTH: 194
<212> TYPE: PRT
<213> ORGANISM: Coccidioides sp.

<400> SEQUENCE: 11

Met Gln Phe Ser His Ala Leu Ile Ala Leu Val Ala Ala Gly Leu Ala
1               5                   10                  15

Ser Ala Gln Leu Pro Asp Ile Pro Pro Cys Ala Leu Asn Cys Phe Val
                20                  25                  30

Glu Ala Leu Gly Asn Asp Gly Cys Thr Arg Leu Thr Asp Phe Lys Cys
            35                  40                  45

His Cys Ser L

```
tttttatttc ccttcctttt ctattttcct ttcttttaat tttcatgctt tcaaactaaa      300
ttcaaattcg agttttgaat ttcagcttct aaattgtaca ctaaaattat atgataaggt      360 aaccccctact attacttta atttttttat tctaccccat attgtttact taggggagaa     420
taattgactt aatcacattc ttcctaggtt tcaattctca atctttcaaa tccacatttt      480
tagatttcta ttttgaattt aaataccagt ttggatttag agttcaattt caaaatacac      540
aaccaaaata ccagcatgaa tgcaaatata ttttatgttt atgtatttac ttttctttta      600
tactttgctc aaaatagtta ttttcatgta tgaaactcaa taagcaagga actcacgtta      660
ttatataacc taataggaat aatttaggta acataattta tcatcctctt gatttaaaag      720
agatatgcct ccagaataag acacatacta aaataactc taatattgaa taactaaagt       780
cgtacaaatc tctactatta ttcctataaa ataataaaga actagctaca acttcttaa      840 ggcattattc agggtttaca gcttgagagg catgaaccca tcctgtatac tcctggactt      900
ggaagacaaa atgtcaacca aagtgaaagg ttttcttatg gttgctgcta agagatagat      960
tgaacactag atctctccta agacgtcagg gcatgcgttt agactcctac acatgcgaaa     1020
actgcatctt acagttggaa gaaactatat ctcaccactt cctgcggtgt aactttgccc     1080
aaagatgttg gctcactgtt ggaatcactc cgccccgaac tttggatcta acgcttgcag     1140
tgctacatat tagagcaaga ctaacaatgc cgtggagaat ggaaggtatt ataaccatgt     1200
catggtgcat atggaaatgt cgaataact ggatattcga aaacataccg ccaacggtgg      1260
cggcctgcaa ggaaatgttc aagactgaaa tgaactacat ctgctaccaa gttaagctcg     1320
agacaggagc taaaagtaga aactggatac aaacactttgt aacatagtga cactccctt    1380 ttcctttctt ttaccttaga actatacata caatccacat tcaataaaaa tttgtaggta     1440
cgccatacac actaccggaa tccggctctt tgccgagtgt gaggcgcttt gtcgagtgct     1500
ttttgtccag cactcggcaa aaagtctttt gccatgtgcc gcactcggca aagtcctgct     1560
ctcggtaacg accgcgttta ccgagagcag gactctcgac acagaaatac actcgacaaa     1620
gaaatctttg ccgagagcca aacactcggc gaacggcagc gctcggcaaa gggtcgtcag     1680
ccgccgtcta aagctgacgg tcgttatctt tgtcgagtgc cccctcgtcc gacactcagt     1740
agagcaagct tgccgagtgc catccttgga cactcgataa agtatatttt atttttttt      1800 attttgccaa ccaaacttt tgtggtatgt tcctacacta tgtagatcta catgtaccat      1860
tttggcacaa ttacaaaaat gttttctata actattagat ttagttcgtt tatttgaatt     1920
tcttcggaaa attcacatat gaactgcaag tcactcgaaa catgaaaaac cgtgcatgca     1980
aaataaatga tatgcatgtt atctagcaca agttacgacc gaattcagaa gcagaccaga     2040
atcttcaagc accatgctca ctaaacatga ccgtgaactt gttatccagt tgtttaaaaa     2100
ttgtataaaa cacaaataaa gtcagaaatt aatgaaactt gtccacatgt catgatatca     2160
tatatagagg ttgtgataaa aatttgataa tgtttcggta aagttgtgac gtactatgtg     2220
tagaaaccta agtgacctac acataaaatc atagagtttc aatgtagttc actcgacaaa     2280
gactttgtca agtgtccgat aaaagtatt cagcaaagaa gccgttgtcg atttactgtt       2340
cgtcgagatc tctttgccga gtgtcacact aggcaaagtc tttacggagt gttttcagg      2400 ctttgacact cggcaaagcg ctcgattcca gtagtgacag taatttgcat caaaaatagc     2460
cgagagattt aaaatgagtc aactaataga ccaactaatt attagctatt agtcgttagc     2520
ttctttaatc taagctaaaa ccaactaata gcttatttgt tgaattacaa ttagctcaac     2580
```

```
ggaattctct gttttttcta taaaaaaaag ggaaactgcc cctcatttac agcaaactgt    2640
ccgctgcctg tcgtccagat acaatgaacg tacctagtag gaactctttt acacgctcgg    2700
tcgctcgccg cggatcggag tcccaggaac acgacaccac tgtggaacac gacaaagtct    2760
gctcagaggc ggccacaccc tggcgtgcac cgagccggag cccggataag cacggtaagg    2820
agagtacggc gggacgtggc gacccgtgtg tctgctgcca cgcagccttc ctccacgtag    2880
ccgcgcggcc gcgccacgta ccagggcccg gcgctggtat aaatgcgcgc cacctccgct    2940
ttagttctgc atacagccaa cccaacacac acccgagcat atcacagtga cagacactac    3000
ac                                                                  3002

<210> SEQ ID NO 13
<211> LENGTH: 2520
<212> TYPE: DNA
<213> ORGANISM: Zea mays

<400> SEQUENCE: 13
gcgctccctg acgctgtctt gggagagctg caagatgaga cactccatcc cgcgcagccc      60
tgtcgtggcg tcctcctgga tggacacctg catcgctgtc gccctccacc aactcacctg     120
aacgaagaat agaataaaaa atggaggagc tgaggggag agtggttgcg ctgtagggag      180
gagagagacc gcgtcattat aagactatct gcaaccgtta cctctaaatt tttccctcta     240
tatcattttt tccccatatt tttccccccta ttttttcatc tcccgcaacg gtttctccta    300
aatactcccc ctatatctca ctaccactat aaaatattat tttttatacc aactatcaat     360
tttttatcta ctaacaatta ctcgtggacc cacagcacag tgtttaggag atgaacagtg     420
acacgctata tctgggggga gagagaaaga ggccggcgcg taggggcgc cgtaggggca      480 ctgctgcggc tgtagagtac cccctacacg ccgcatgcaa gggaaggggg ctgtcagggg     540
ggcaatgttg cgcatagcct aaagagcgga tgaagcggct gcaatttgc acgctggatt      600 cataaatagt gcatattact aaaaaaaagg gtggggatag gtatagagag tctattagag     660
ttgatctaag acccggttta tttcagatta taatctgtcc ggattatata atccagcgca     720
aataatacag taggtaaaca aacaactaga ttatgggttc agattatata atctaaaccc     780
cagattatga taatctcata atctcctcaa gagtagctta ttggagatta ttttggcaaa     840
agacccacta cccatggtta tgtaaataga aattataata tatatcatct tttttctcac     900
cttaaataaa caaataaggg tattgttgtc tttatgaata atctacattt gtataatcta     960
aactaccaaa caactacatc tagattataa tctggattat ataattttaa ttataatcta    1020
gattatataa tttataagct gaaacaaccc ggccctaaag cactatcgta tcacctatct    1080
gaaataagtc acgggtttcg aacgtccact tgcgtcgcac ggaattgcat gtttcttgtt    1140
ggaagcatat tcacgcaatc tccacacata aaggtttatg tataaactta catttagctc    1200
agtttaatta cagtcttatt tggatgcata tgtatggttc tcaatccata taagttagag    1260
taaaaaataa gtttaaattt tatcttaatt cactccaaca tatatggatt gagtacaata    1320
ctcatgtgca tccaaacaaa ctacttatat tgaggtgaat ttggatagaa attaaactaa    1380
cttacacact aagccaatct ttactatatt aaagcaccag tttcaacgat cgtcccgcgt    1440
caatattatt aaaaaactcc tacatttctt tataatcaac ccgcactctt ataatctctt    1500
ctctactact ataataagag agtttatgta caaataagg tgaaattatg tataagtgtt    1560
ctggatattg gttgttggct ccatattcac acaacctaat caatagaaaa catatgttttt    1620 attaaaacaa aatttatcat atatcatata tatatatata aaccgtagca atgcacgggc    1680
```

```
atataactag tgcaacttaa tacatgtgtg tattaagatg aataagaggg tatccaaata    1740
aaaaacttgt tcgcttacgt ctggatcgaa aggggttgga aacgattaaa tctcttccta    1800
gtcaaaattg aatagaagga gatttaatct ctcccaatcc ccttcgatca tccaggtgca    1860
accgtataag tcctaaagtg gtgaggaaca cgaaacaacc atgcattggc atgtaaagct    1920
ccaagaattt gttgtatcct taacaactca cagaacatca accaaaattg cacgtcaagg    1980
gtattgggta agaaacaatc aaacaaatcc tctctgtgtg caaagaaaca cggtgagtca    2040
tgccgagatc atactcatct gatatacatg cttacagctc acaagacatt acaaacaact    2100
catattgcat tacaaagatc gtttcatgaa aaataaaata ggccggacag gacaaaaatc    2160
cttgacgtgt aaagtaaatt tacaacaaaa aaaagccat atgtcaagct aaatctaatt     2220
cgttttacgt agatcaacaa cctgtagaag gcaacaaaac tgagccacgc agaagtacag    2280
aatgattcca gatgaaccat cgacgtgcta cgtaaagaga gtgacgagtc atatacattt    2340
ggcaagaaac catgaagctg cctacagccg tctcggtggc ataagaacac aagaaattgt    2400
gttaattaat caaagctata aataacgctc gcatgcctgt gcacttctcc atcaccacca    2460
ctgggtcttc agaccattag ctttatctac tccagagcgc agaagaaccc gatcgacacc    2520
```

<210> SEQ ID NO 14
<211> LENGTH: 6510
<212> TYPE: DNA
<213> ORGANISM: Zea mays

<400> SEQUENCE: 14

```
ggcgcgccgg tatgaatttg gaaacaaatt cagtactttt aaaaaaattt gttgtaggga      60
gcaaataata cataaaataa tttatgcatt atttttatttt ttatttgtaa taatatgctt    120
gaaacgataa ttcagtatgc atgttgtgcc agtgtactac acgggcgggg ggagggattt     180
gagtgggcca gcgcggtgcg tagggtagat gggctgaaat tgataactca agtccgacta    240
ggttctcttt ttatttccct tccttttcta ttttccttc ttttaatttt catgctttca     300
aactaaattc aaattcgagt tttgaattc agcttctaaa ttgtacacta aaattatatg     360
ataaggtaac ccctactatt acttttaatt tttttattct accccatatt gtttacttag    420
gggagaataa ttgacttaat cacattcttc ctaggtttca attctcaatc tttcaaatcc    480
acatttttag atttctattt tgaatttaaa taccagtttg gatttagagt tcaatttcaa    540
aatacacaac caaatacca gcatgaatgc aaatatattt tatgtttatg tatttacttt      600
tcttttatac tttgctcaaa atagttattt tcatgtatga aactcaataa gcaaggaact    660
cacgttatta tataacctaa taggaataat ttaggtaaca taatttatca tcctcttgat    720
ttaaaagaga tatgcctcca gaataagaca catactaaaa ataactctaa tattgaataa    780
ctaaagtcgt acaaatctct actattattc ctataaaata ataagaact agctacaact    840 tctttaaggc attattcagg gtttacagct tgagaggcat gaacccatcc tgtatactcc    900
tggacttgga agacaaaatg tcaaccaaag tgaaaggttt tcttatggtt gctgctaaga    960
gatagattga acactagatc tctcctaaga cgtcagggca tgcgtttaga ctcctacaca   1020
tgcgaaaact gcatcttaca gttggaagaa actatatctc accattcct gcggtgtaac     1080 tttgcccaaa gatgttggct cactgttgga atcactccgc cccgaacttt ggatctaacg   1140
cttgcagtgc tacatattag agcaagacta acaatgccgt ggagaatgga aggtattata   1200
accatgtcat ggtgcatatg gaaatgtcga ataactgga tattcgaaaa cataccgcca     1260
```

```
acggtggcgg cctgcaagga aatgttcaag actgaaatga actacatctg ctaccaagtt   1320
aagctcgaga caggagctaa aagtagaaac tggatacaac actttgtaac atagtgacac   1380
tccccttttc ctttctttta ccttagaact atacatacaa tccacattca ataaaaattt   1440
gtaggtacgc catacacact accggaatcc ggctctttgc cgagtgtgag gcgctttgtc   1500
gagtgctttt tgtccagcac tcggcaaaaa agtctttgcc atgtgccgca ctcggcaaag   1560
tcctgctctc ggtaacgacc gcgtttaccg agagcaggac tctcgacaca gaaatacact   1620
cgacaaagaa atctttgccg agagccaaac actcggcgaa cggcagcgct cggcaaaggg   1680
tcgtcagccg ccgtctaaag ctgacggtcg ttatctttgt cgagtgcccc ctcgtccgac   1740
actcagtaga gcacgcgccg gtatgaattt ggaaacaaat tcagtacttt taaaaaaatt   1800
tgttgtaggg agcaaataat acataaaata atttatgcat tattttattt tttatttgta   1860
ataatatgct tgaaacgata attcagtatg catgttgtgc cagtgtacta cacgggcggg   1920
gggagggggat tgagtgggcc agcgcggtgc gtagggtaga tgggctgaaa ttgataactc   1980
aagtccgact aggttctctt tttatttccc ttccttttct attttccttt cttttaattt   2040
tcatgctttc aaactaaatt caaattcgag ttttgaattt cagcttctaa attgtacact   2100
aaaattatat gataaggtaa cccctactat tacttttaat ttttttattc taccccatat   2160
tgtttactta ggggagaata attgacttaa tcacattctt cctaggtttc aattctcaat   2220
ctttcaaatc cacattttta gatttctatt ttgaatttaa ataccagttt ggatttagag   2280
ttcaatttca aaatacacaa ccaaaatacc agcatgaatg caaatatatt ttatgtttat   2340
gtatttactt ttctttttata ctttgctcaa aatagttatt ttcatgtatg aaactcaata   2400
agcaaggaac tcacgttatt atataaccta ataggaataa tttaggtaac ataatttatc   2460
atcctcttga tttaaaagag atatgcctcc agaataagac acatactaaa aataactcta   2520
atattgaata actaaagtcg tacaaatctc tactattatt cctataaaat aataaagaac   2580
tagctacaac ttctttaagg cattattcag ggtttacagc ttgagaggca tgaacccatc   2640
ctgtatactc ctggacttgg aagacaaaat gtcaaccaaa gtgaaaggtt ttcttatggt   2700
tgctgctaag agatagattg aacactagat ctctcctaag acgtcagggc atgcgtttag   2760
actcctacac atgcgaaaac tgcatcttac agttggaaga aactatatct caccacttcc   2820
tgcggtgtaa ctttgcccaa agatgttggc tcactgttgg aatcactccg ccccgaactt   2880
tggatctaac gcttgcagtg ctacatatta gagcaagact aacaatgccg tggagaatgg   2940
aaggtattat aaccatgtca tggtgcatat ggaaatgtcg aaataactgg atattcgaaa   3000
acataccgcc aacggtggcg gcctgcaagg aaatgttcaa gactgaaatg aactacatct   3060
gctaccaagt taagctcgag acaggagcta aagtagaaa ctggatacaa cactttgtaa   3120
catagtgaca ctccccttttt cctttctttt accttagaac tatacataca atccacattc   3180
aataaaaatt tgtaggtacg ccatacacac taccggaatc cggctctttg ccgagtgtga   3240
ggcgctttgt cgagtgcttt ttgtccagca ctcggcaaaa agtctttgc catgtgccgc   3300
actcggcaaa gtcctgctct cggtaacgac cgcgtttacc gagagcagga ctctcgacac   3360
agaaatacac tcgacaaaga atctttgccg gagagccaaa cactcggcga acggcagcgc   3420
tcggcaaagg gtcgtcagcc gccgtctaaa gctgacggtc gttatctttg tcgagtgccc   3480
cctcgtccga cactcagtag agcacgcgcc ggtatgaatt tggaaacaaa ttcagtactt   3540
ttaaaaaaat ttgttgtagg gagcaaataa tacataaaat aatttatgca ttattttatt   3600
ttttatttgt aataatatgc ttgaaacgat aattcagtat gcatgttgtg ccagtgtact   3660
```

-continued

```
acacgggcgg ggggagggga ttgagtgggc cagcgcggtg cgtagggtag atgggctgaa      3720
attgataact caagtccgac taggttctct ttttatttcc cttccttttc tattttcctt      3780
tcttttaatt ttcatgcttt caaactaaat tcaaattcga gttttgaatt tcagcttcta      3840
aattgtacac taaaattata tgataaggta acccctacta ttacttttaa tttttttatt      3900
ctaccccata ttgtttactt aggggagaat aattgactta atcacattct tcctaggttt      3960
caattctcaa tctttcaaat ccacattttt agatttctat tttgaattta aataccagtt      4020
tggatttaga gttcaatttc aaaatacaca accaaaatac cagcatgaat gcaaatatat      4080
tttatgttta tgtatttact tttcttttat actttgctca aaatagttat tttcatgtat      4140
gaaactcaat aagcaaggaa ctcacgttat tatataacct aataggaata atttaggtaa      4200
cataatttat catcctcttg atttaaaaga gatatgcctc cagaataaga cacatactaa      4260
aaataactct aatattgaat aactaaagtc gtacaaatct ctactattat tcctataaaa      4320
taataaagaa ctagctacaa cttctttaag gcattattca gggtttacag cttgagaggc      4380
atgaacccat cctgtatact cctggacttg gaagacaaaa tgtcaaccaa agtgaaaggt      4440
tttcttatgg ttgctgctaa gagatagatt gaacactaga tctctcctaa gacgtcaggg      4500
catgcgttta gactcctaca catgcgaaaa ctgcatctta cagttggaag aaactatatc      4560
tcaccacttc ctgcggtgta actttgccca aagatgttgg ctcactgttg gaatcactcc      4620
gccccgaact ttggatctaa cgcttgcagt gctacatatt agagcaagac taacaatgcc      4680
gtggagaatg gaaggtatta taaccatgtc atggtgcata tggaaatgtc gaaataactg      4740
gatattcgaa aacataccgc caacggtggc ggcctgcaag gaaatgttca agactgaaat      4800 gaactcatc tgctaccaag ttaagctcga gacaggagct aaaagtagaa actggataca      4860
acactttgta acatagtgac actccccttt tcctttcttt taccttagaa ctatacatac      4920
aatccacatt caataaaaat ttgtaggtac gccatacaca ctaccggaat ccggctcttt      4980
gccgagtgtg aggcgctttg tcgagtgctt tttgtccagc actcggcaaa aaagtctttg      5040
ccatgtgccg cactcggcaa agtcctgctc tcggtaacga ccgcgtttac cgagagcagg      5100
actctcgaca cagaaataca ctcgacaaag aaatctttgc cgagagccaa acactcggcg      5160
aacggcagcg ctcggcaaag ggtcgtcagc cgccgtctaa agctgacggt cgttatcttt      5220
gtcgagtgcc ccctcgtccg acactcagta gagcaagctt gccgagtgcc atccttggac      5280
actcgataaa gtatatttta ttttttttta тттгтgссaaс caaactттттт gtggtatgtt      5340 cctacactat gtagatctac atgtaccatt ttggcacaat tacaaaaatg ttttctataa      5400
ctattagatt tagттcgтттт atttgaattt cttcggaaaa ttcacatatg aactgcaagt      5460
cactcgaaac atgaaaaacc gtgcatgcaa aataaatgat atgcatgtta tctagcacaa      5520
gttacgaccg aattcagaag cagaccagaa tcttcaagca ccatgctcac taaacatgac      5580
cgtgaacttg ttatccagtt gtttaaaaat tgtataaaac acaataaag tcagaaatta      5640 atgaaacttg tccacatgtc atgatatcat atatagaggt tgtgataaaa atttgataat      5700
gtttcggtaa agttgtgacg tactatgtgt agaaacctaa gtgacctaca cataaaatca      5760
tagagtttca atgtagttca ctcgacaaag actttgtcaa gtgtccgata aaagtattc      5820 agcaaagaag ccgttgtcga tttactgttc gtcgagatct ctttgccgag tgtcacacta      5880
ggcaaagtct ttacggagtg tttttcaggc tttgacactc ggcaaagcgc tcgattccag      5940
tagtgacagt aatttgcatc aaaaatagcc gagagattta aatgagtca actaatagac      6000
```

-continued

```
caactaatta ttagctatta gtcgttagct tctttaatct aagctaaaac caactaatag   6060
cttatttgtt gaattacaat tagctcaacg gaattctctg tttttctat aaaaaaaagg    6120 gaaactgccc ctcatttaca gcaaactgtc cgctgcctgt cgtccagata caatgaacgt   6180
acctagtagg aactctttta cacgctcggt cgctcgccgc ggatcggagt cccaggaaca   6240
cgacaccact gtggaacacg acaaagtctg ctcagaggcg gccacaccct ggcgtgcacc   6300
gagccggagc ccggataagc acggtaagga gagtacggcg ggacgtggcg acccgtgtgt   6360
ctgctgccac gcagccttcc tccacgtagc cgcgcggccg cgccacgtac cagggcccgg   6420
cgctggtata aatgcgcgcc acctccgctt tagttctgca tacagccaac ccaacacaca   6480
cccgagcata tcacagtgac agacactaca                                    6510
```

<210> SEQ ID NO 15
<211> LENGTH: 72
<212> TYPE: DNA
<213> ORGANISM: Hordeum vulgare

<400> SEQUENCE: 15

```
atggccaaca agcacctgag cctctccctc ttcctcgtgc tcctcggcct ctccgcctcc     60
ctcgccagcg gc                                                         72
```

<210> SEQ ID NO 16
<211> LENGTH: 129
<212> TYPE: DNA
<213> ORGANISM: Hordeum vulgare

<400> SEQUENCE: 16

```
atggcccacg cccgcgtcct cctcctggcg ctcgccgtgc tggccacggc cgccgtcgcc     60
gtcgcctcct ctagctcctt cgccgactcc aacccgatcc ggccggtcac cgaccgcgcc    120
gcgtccacc                                                            129
```

<210> SEQ ID NO 17
<211> LENGTH: 12
<212> TYPE: DNA
<213> ORGANISM: Artificial Sequence
<220> FEATURE:
<223> OTHER INFORMATION: Endoplasmic reticulum signal sequence

<400> SEQUENCE: 17

```
aaggacgagc tc                                                         12
```

<210> SEQ ID NO 18
<211> LENGTH: 585
<212> TYPE: DNA
<213> ORGANISM: Coccidioides sp.

<400> SEQUENCE: 18

```
atgcagttct ctcacgctct catcgctctc gtcgctgccg gcctcgccag tgcccagctc     60
ccagacatcc caccttgcgc tctcaactgc ttcgttgagg ctctcggcaa cgatggctgc    120
actcgcttga ccgacttcaa gtgccactgc tccaagcctg agctcccagg acagatcact    180
ccttgcgttg aggaggcctg ccctctcgac gcccgtatct ccgtctccaa catcgtcgtt    240
gaccagtgct ccaaggccgg tgtcccaatt gacatcccac cagttgacac caccgccgct    300
cccgagccat ccgagaccgc tgagcccacc gctgagccaa ccgaggagcc cactgccgag    360
cctaccgctg agcccaccgc tgagccgact catgagccca ccgaggagcc cactgccgtc    420
ccaaccggca ctggcggtgg tgtccccact ggcaccggtt ccttcaccgt cactggcaga    480
```

```
ccaactgcct ccaccccagc tgagttccca ggtgctggct ccaacgtccg tgccagcgtt    540
ggcggcattg ctgctgctct cctcggtctc gctgcctacc tgtaa                   585
```